US012085570B2

(12) United States Patent
Yang et al.

(10) Patent No.: US 12,085,570 B2
(45) Date of Patent: Sep. 10, 2024

(54) BIOMARKERS FOR LUNG CANCER STEM CELLS

(71) Applicant: National Taiwan University, Taipei (TW)

(72) Inventors: Pan-Chyr Yang, Taipei (TW); Huei-Wen Chen, Taipei (TW); Wan-Jiun Chen, Taipei (TW)

(73) Assignee: NATIONAL TAIWAN UNIVERSITY, Taipei (TW)

( * ) Notice: Subject to any disclaimer, the term of this patent is extended or adjusted under 35 U.S.C. 154(b) by 1100 days.

(21) Appl. No.: 16/475,957

(22) PCT Filed: Jan. 3, 2018

(86) PCT No.: PCT/CN2018/070383
§ 371 (c)(1),
(2) Date: Jul. 3, 2019

(87) PCT Pub. No.: WO2018/127055
PCT Pub. Date: Jul. 12, 2018

(65) Prior Publication Data
US 2019/0346445 A1    Nov. 14, 2019

Related U.S. Application Data

(60) Provisional application No. 62/442,077, filed on Jan. 4, 2017.

(51) Int. Cl.
*C12Q 1/6886* (2018.01)
*G01N 33/574* (2006.01)

(52) U.S. Cl.
CPC ..... *G01N 33/57423* (2013.01); *C12Q 1/6886* (2013.01); *G01N 33/57419* (2013.01); *G01N 33/57438* (2013.01); *G01N 33/57492* (2013.01); *C12Q 2600/112* (2013.01); *G01N 2333/70585* (2013.01); *G01N 2333/70596* (2013.01); *G01N 2800/56* (2013.01)

(58) Field of Classification Search
CPC ............ C12Q 1/6886; C12Q 2600/112; C12Q 2600/118; C12Q 2600/158; G01N 33/57423; G01N 2333/70585
See application file for complete search history.

(56) References Cited

U.S. PATENT DOCUMENTS

2012/0071350 A1    3/2012  Damelin et al.

FOREIGN PATENT DOCUMENTS

| AU | 2013203260 A1 | 9/2013 |
| CN | 105102614 A | 11/2015 |

(Continued)

OTHER PUBLICATIONS

Feng et al., CD14(+)S100A9(+) monocytic myeloid-derived suppressor cells and their clinical relevance in non-small cell lung cancer. Am J Respir Crit Care Med. Nov. 15, 2012; 186(10):1025-36. Epub Sep. 6, 2012.

(Continued)

*Primary Examiner* — Diana B Johannsen
(74) *Attorney, Agent, or Firm* — Mintz, Levin, Cohn, Ferris, Glovsky and Popeo, P.C.

(57) ABSTRACT

Provided herein are methods and kits for analyzing a sample such as a biological sample obtained from a subject having, suspected of having, or being at risk for a cancer to assess presence of cancer stem cells in the sample, which is indicative of poor cancer prognosis.

12 Claims, 13 Drawing Sheets

Specification includes a Sequence Listing.

(56) References Cited

FOREIGN PATENT DOCUMENTS

| CN | 106053821 A | 10/2016 |
|---|---|---|
| WO | 0212447 A2 | 2/2002 |
| WO | WO 2002/12447 A2 | 2/2002 |
| WO | 2013126993 A1 | 9/2013 |

OTHER PUBLICATIONS

Huang et al., Increased CD14(+)HLA-DR (−/low) myeloid-derived suppressor cells correlate with extrathoracic metastasis and poor response to chemotherapy in non-small cell lung cancer patients. Cancer Immunol Immunother. Sep. 2013;62(9):1439-51. Epub Jun. 13, 2013.

Maeda et al., Circulating CD14+CD204+ cells predict postoperative recurrence in non-small-cell lung cancer patients. J Thorac Oncol. Feb. 2014;9(2):179-88.

MacDonagh et al., Lung cancer stem cells: The root of resistance. Cancer Lett. Mar. 28, 2016;372(2):147-56. Epub Jan. 18, 2016.

Leung, E.L., et al. "Non-Small Cell Lung Cancer Cells Expressing CD44 Are Enriched for Stem Cell-Like Properties"; PLOS One.; vol. 5, No. 11; Nov. 19, 2010; pp. 1-13.

Lobba, A.R.M, et al. "Differential Expression of CD90 and CD14 Stem Cell Markers in Malignant Breast Cancer Cell Lines"; Cytometry PartA.' vol. 81A; Oct. 22, 2012; pp. 1084-1091.

A

B

BIOMARKERS FOR LUNG CANCER STEM CELLS

CROSS-REFERENCE TO RELATED APPLICATIONS

The present application is a national stage filing under 35 U.S.C. § 371 of PCT International Application No. PCT/CN2018/070383, filed Jan. 3, 2018, which claims priority under 35 U.S.C. § 119(e) to U.S. Provisional Application No. 62/442,077, filed Jan. 4, 2017, the entire contents of each of which is are incorporated by reference herein in their entirety.

BACKGROUND

Lung cancer is the most common fatal malignancy worldwide and non-small cell lung cancer (NSCLC) is the most common type of lung cancer. Because of the success of driver gene identification and specific targeted therapy, many lung cancer patients show good initial responses to treatment. However, most patients eventually develop drug resistance and relapse within a year.

Traditional anticancer treatment strategies target cancer cells of an unspecified type. However, solid tumors such as lung cancer often comprise an organized, heterogeneous cell population. The complicated cell-cell interactions that form the tumor microenvironment (or niche) involve a small population of cells termed cancer stem cells (CSCs), which may cause most malignant tumors. Both CSCs and the tumor niche play major roles in cancer recurrence, metastasis and drug resistance.

It is therefore of great interest to identify biomarkers for CSCs and develop reliable diagnostic and prognostic methods for identifying subjects having cancer (e.g., lung cancer), for example, cancer associated with poor prognosis. Such biomarkers would also benefit studies on lung cancer mechanisms, which could facilitate the development of effective new therapies for lung cancer.

SUMMARY OF THE PRESENT DISCLOSURE

The present disclosure is based, at least in part, on the identification of new biomarkers of cancer stem cells (e.g., lung cancer stem cells), for example, CD14 or a combination of CD14 and CD44. CD14, as well as CD44, have been found to be differentially present in cancer-associated fibroblast (CAF) co-cultured lung cancer stem cells as compared to the differentiated cancer cells via transcriptomic and proteomic analysis. Further, CD14 and CD44 were found to correlate with poor prognosis in lung cancer patients. In addition, CD14 was also found to present in various types of cancer cells, including liver cancer, colon cancer, and pancreatic cancer.

Accordingly, one aspect of the present disclosure provides a method for analyzing a sample, comprising: (i) providing a sample suspected of containing cancer stem cells, and (ii) measuring the level of CD14, and optionally also the level of CD44, in the sample.

In some embodiments, the method comprises measuring the level of CD14 protein, the level of CD44 protein, or both. In some examples, the level of membrane-bound CD14 protein and/or the level of membrane-bound CD44 in the sample are measured. In other embodiments, the level of circulating (soluble) CD14 and/or the level of circulating (soluble) CD44 in the sample are measured. The protein levels of CD14 and/or CD44 may be measured by an immunohistochemical assay, an immunoblotting assay, ELISA, or a flow cytometry assay.

In some embodiments, the method comprises measuring the level of a nucleic acid encoding CD14, the nucleic acid encoding CD44, or both. In some embodiments, the level of the CD14-encoding nucleic acid, the level of CD44-encoding nucleic acid, or both are measured by a real-time reverse transcriptase PCR (RT-PCR) assay or a nucleic acid microarray assay.

The sample to be analyzed in any of the assay methods described herein can be a biological sample of a human patient having or suspected of having a cancer, for example, lung cancer (e.g., non-small cell lung cancer or NSCLC), liver cancer, colon cancer, or pancreatic cancer. In some embodiments, the biological sample is a tissue sample, which may be obtained from a human patient as described herein, for example, from a tumor site or a suspected tumor site. In other embodiments, the biological sample is a body fluid sample from the human patient as described herein.

Any of the assay methods described herein may further comprise determining presence of cancer stem cells (e.g., lung cancer stem cells, liver cancer stem cells, colon cancer stem cells or pancreatic stem cells) in the sample based on the level of CD14, the level of CD14, or a combination of CD14 and CD44. An elevated level of CD14, an elevated level of CD44, or an elevated level of CD14 and CD44 is indicative of presence of cancer stem cells in the sample.

Alternatively or in addition, any of the assay methods described herein may further comprise determining survival rate of the human patient from whom the biological sample is obtained. An elevated level of CD14, an elevated level of CD44, or an elevated level of CD14 and CD44 is indicative of poor survival rate. In some embodiments, the method further comprises subjecting the human patient to a treatment for cancer, for example, a treatment for lung cancer (e.g., NSCLC), a treatment for liver cancer, a treatment for colon cancer, or a treatment of pancreatic cancer.

In another aspect, a method is provided for detecting a cancer associated with poor prognosis, comprising: (i) providing a sample of a subject having cancer, (ii) measuring the level of CD14 in the sample, and optionally also the level of CD44, and (iii) determining whether the subject has a cancer associated with poor prognosis based on the level of CD14 or the level of both CD14 and CD44 in the sample. The subject is identified as having a cancer associated with poor prognosis if the level of CD14, or the level of both CD14 and CD44 in the sample is higher than a predetermined level. In some examples, the cancer can be lung cancer (e.g., NSCLC), liver cancer, colon cancer, or pancreatic cancer.

In another aspect, a method is provided for enriching cancer stem cells (e.g., those described herein), the method comprising: (i) providing a sample suspected of containing lung cancer stem cells, and (ii) isolating from the sample $CD14^+$ cells and optionally $CD14^+/CD44^{Hi}$ cells. Also provided herein are uses of one or more detecting agents for measuring the level of CD14 and optionally the level of CD44 for cancer prognosis in a subject, wherein the cancer prognosis can be performed by any of the assay methods described herein.

The details of one or more embodiments of the present disclosure are set forth in the description below. Other features or advantages of the present disclosure will be apparent from the following drawings and detailed description of several embodiments, and also from the appended claims.

BRIEF DESCRIPTION OF DRAWINGS

The following drawings form part of the present specification and are included to further demonstrate certain aspects of the present disclosure, which can be better understood by reference to one or more of these drawings in combination with the detailed description of specific embodiments presented herein.

DETAILED DESCRIPTION

Figure 1:
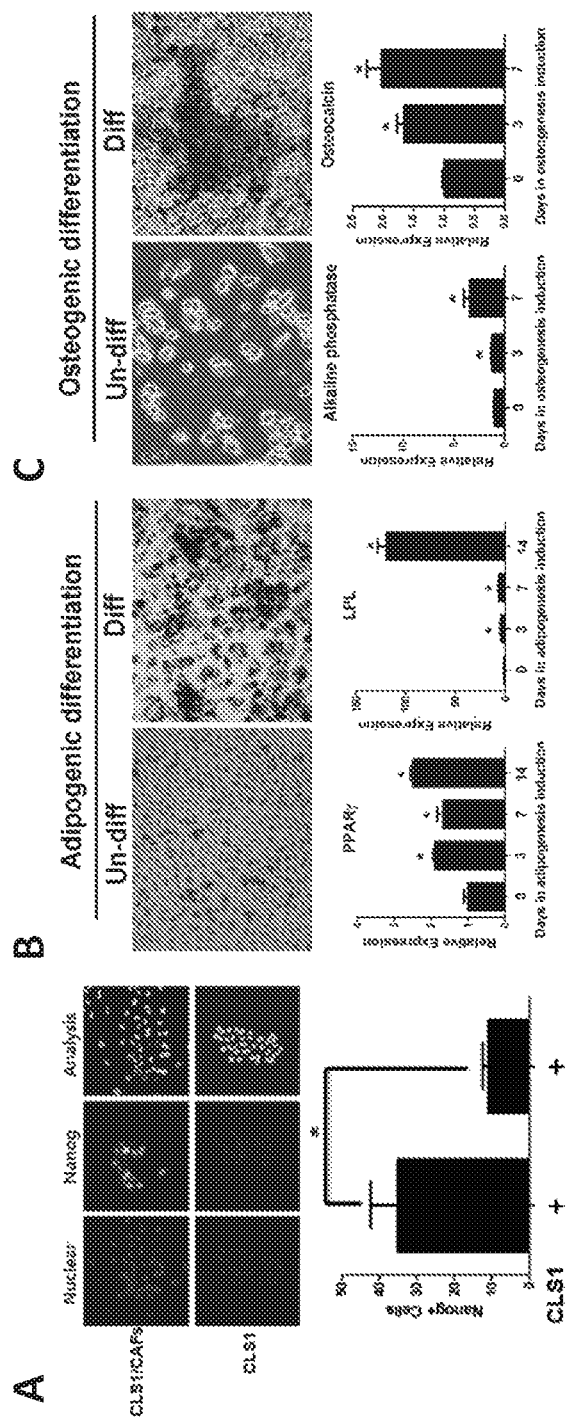
FIG. 1 shows that CD14 and CD44 are involved in maintaining the stemness of lung cancer stem cells (LCSCs). A: Nanog-positive stem cells per colony were analyzed through image-based high-content analysis. CLS1 cells were co-cultured with CAFs or without CAFs (N=4). Scale bar, 5004. Upper panel: image photos; Lower panel: quantitative chart. B: Following adipogenic differentiation, CLS1/CAFs cells stained positive with oil red O dye, which stains oil droplets (upper panel). RT Q-PCR analysis of the adipocyte marker PPARy and LPL in CLS1/CAFs cells subjected to adipocyte differentiation at different time points as indicated in the figure (lower panel). C: Following osteogenic differentiation, CLS1/CAFs cells stained positive with alizarin red S which stains for calcium deposits (upper panel). RT Q-PCR analysis of the osteoblast marker alkaline phosphatase and osteocalcin in CLS1/CAFs cells subjected to osteoblast differentiation at different time points as indicated in the figure (lower panel). D: The incidence of mouse xenograft tumors from CLS1/CAF co-cultures (N≥3 mice), differentiated CLS1 cells (N≥3 mice) was determined following the subcutaneous injection of different cell numbers ($1\times10^4$, $1\times10^3$, $1\times10^2$ and 10 cells) into NSG mice. The tumor-initiating frequency of CSCs (TIF) was calculated using the L-calclimiting dilution analysis software. CI, confidence interval. E: A schematic illustration of the cancer stem cell markers screening strategy. CSCs/CAFs and differentiated cancer cell (CLS1 p.6) were performed the Affymetrix microarray and membrane proteomics to identify the CSCs/CAFs highly expressed surface proteins. The candidate marker were be correlated with patient's survival via published cohort. F: The patients were designated as having high or low CD44 and CD14 expression (cut-off value=median risk score). The results showed a significant difference in the Kaplan-Meier estimates of relapse-free survival between the high and low expression groups. P values were obtained from two-sided log-rank tests. By combining the expression levels of CD44 and CD14 in cancer cells, the patients were divided into three groups: a high CD44/high CD14 group, a low CD44/low CD14 group and others. The results showed a significant difference in Kaplan-Meier estimates of overall and relapse-free survival. P values were obtained from 2-sided log-rank tests.
Figure 1:
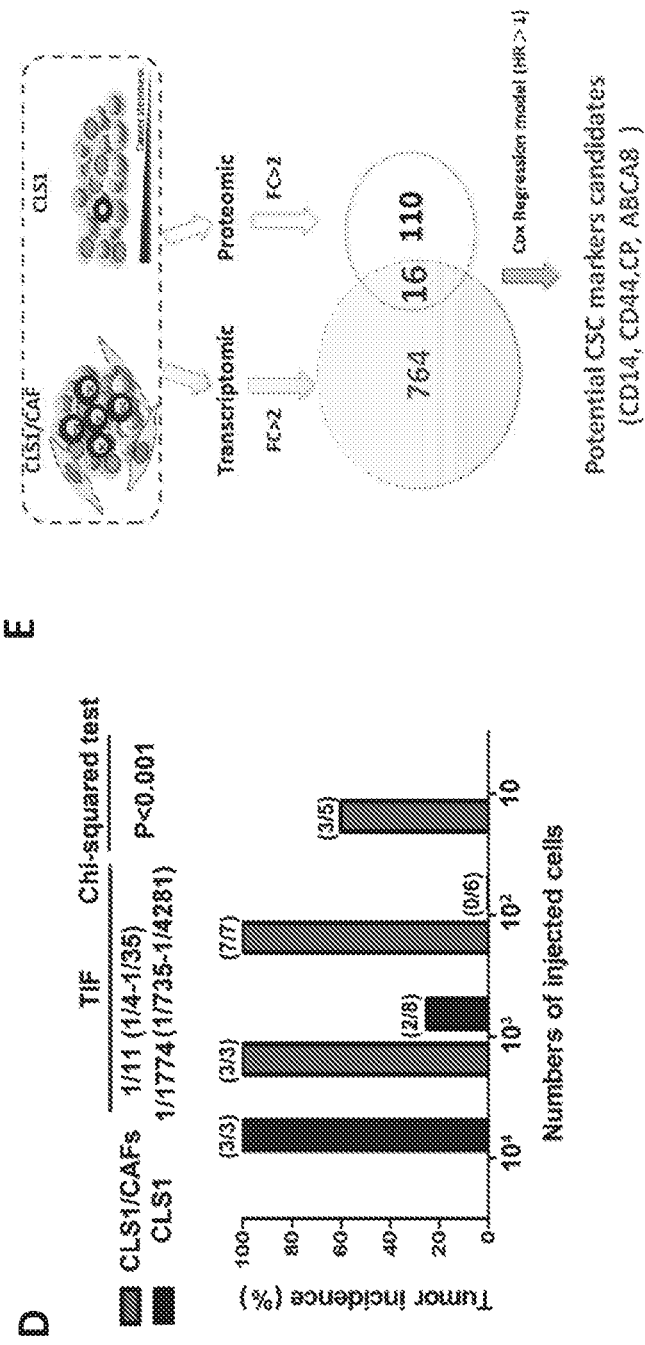
Figure 1:
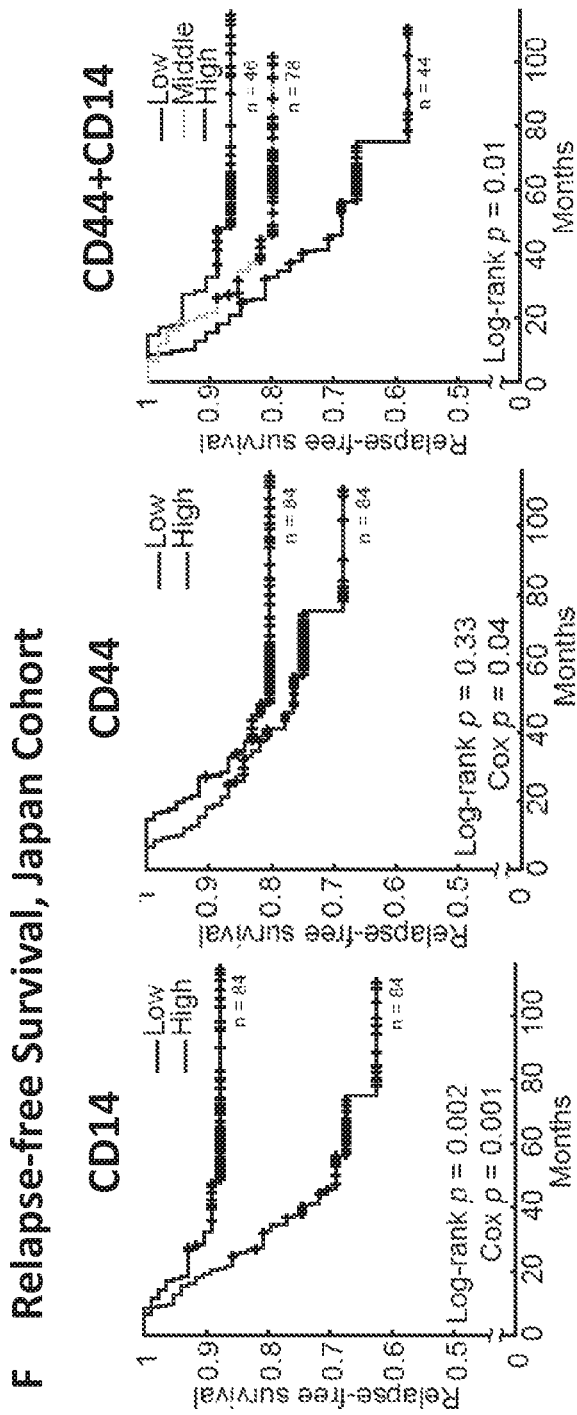

Cancer stem cells (CSCs) represent a sub-population of tumorigenic stem cell-like, multi-potent cells. CSCs are capable of self-renewal, differentiating into specialized cell types, and/or developing into cancer. The phenotype of "cancer sternness" may be the driving force behind carcinogenesis. CSCs are suggested to contribute to chemo- or radio-resistance and/or metastasis. Increasing evidence shows that CSCs are present in leukaemia and in various solid tumors, including lung cancer. To maintain "stemness," most stem cells depend on direct contact in the microenvironment or crosstalk with "feeder cells" such as fibroblasts. Under the context of cancer, CSCs may depend on direct contact with cancer-associated fibroblasts (CAFs) to maintain stemness. Such interactions may create a niche for tumor growth and/or metastasis.

The present disclosure is based, at least in part, on the identification of markers, including CD14 and CD44, which are highly expressed in CAF co-cultured CSCs via transcriptomic and proteomic analysis. For example, CD14 is identified as new biomarker of CSCs (e.g., CSCs of lung cancer, liver cancer, colon cancer, or pancreatic cancer). It was determined that CSCs showed higher expression levels of cell surface protein biomarkers (e.g., CD14 and CD44) than differentiated cancer cells. Accordingly, the level of such protein biomarkers (e.g., CD14 and CD44) correlated with presence and/or level of CSCs and thus poor prognosis in tumor specimens from cancer patients.

Thus, some aspects of the present disclosure provide methods for analyzing samples such as biological samples suspected of containing cancer stem cells based on the level of CD14 and optionally also the level of CD44 (either membrane-bound or circulating molecules (soluble CD14 or soluble CD44). Such assay methods may be useful for clinical purposes e.g., for determining presence of cancer stem cells in the sample, which may be indicative of poor cancer prognosis, selecting a candidate for treatment based on presence/level of cancer stem cells, monitoring cancer progression, assessing the efficacy of a treatment against the cancer, determining a course of treatment, assessing whether a subject is at risk for a relapse of the cancer. The assay methods described herein may also be useful for non-clinical applications, for example, for research purposes, including, e.g., studying the mechanism of cancer development and metastasis and/or biological pathways/processes involved in cancer, and developing new therapies for cancer based on such studies.

Assay Methods for Determining Cancer Stem Cell (CSC) Biomarkers

Provided herein are assay methods for analyzing samples to determine presence and/or level of biomarkers that may be associated with cancer stem cells.

(i) Biomarkers for CSC

As used herein, the term "biomarker" or "biomarker set" indicative of a specific population of cells (e.g., CSCs) refers to a biological molecule (e.g., a protein) or set of such biological molecules that are present at a level in that specific population of cells that deviates from a level of the same molecule(s) in a different population of cells. For example, a biomarker that is indicative of CSCs may have an elevated level of a reduced level in CSCs as relative to the level of the same marker in differentiated cancer cells of the same type or in non-cancer cells. The CSC biomarkers described herein may have a level in CSCs that deviates from (enhanced or reduced) the level of the same marker in differentiated cancer cells of the same type or in non-cancer cells by at least 20% (e.g., 30%, 50%, 80%, 100%, 2-fold, 5-fold, 10-fold, 20-fold, 50-fold, 100-fold or more). Such biomarker/biomarker sets may be used in both diagnostic/prognostic applications and non-clinical applications (for example, for research purposes).

In some examples, the biomarker comprises CD14. CD14, a glycoprotein, is a co-receptor for bacterial lipopolysaccharide (LPS) and binds LPS in the presence of lipopolysaccharide-binding protein (LBP). There are two isoforms of CD14, a membrane-bound form (mCD14) and a soluble form (sCD14). Either form can serve as a biomarker for cancer stem cells. The amino acid sequences of human mCD14 and sCD14 are provided in GenBank accession number NP 001167575.0, PDB: 4GLP_A, UniGene: Hs.163867, and GeneCards GCID: GC05M140594.

Alternative or in addition, the biomarker may comprise CD44. CD44 is a cell-surface glycoprotein involved in cell-cell interactions, cell adhesion and migration. It is a receptor for hyaluronic acid and can also interact with other ligands, such as osteopontin, collagens, and matrix metalloproteinases (MMPs). The amino acid sequence of human CD44 is provided in GenBank accession number ACI46596.1.

In addition to CD14 and CD44, CP and ABCA8 were also found to be differentially present in cancer stem cells as compared with CAFs and thus can be used as markers in the assay methods described herein.

Exemplary biomarkers indicative of cancer stem cells (e.g., lung cancer stem cells, liver cancer stem cells, colon cancer stem cells, or pancreatic cancer stem cells) are provided in Table 1 below.

TABLE 1

| | | Cancer Stem Cell Markers | | | |
|---|---|---|---|---|---|
| | | Clinical relevance | | CLS1/CAF/CLS1p.6 | |
| Gene Symbol | Description | Hazard Ratio | P value | Protein Level | RNA Level |
| CD14 | Monocyte differentiation antigen CD14 | 1.45 | $1.23 \times 10^{-3}$ | 2.2 | 3.1 |
| CD44 | CD44 molecule (Indian blood group) | 1.29 | $3.69 \times 10^{-2}$ | 3.2 | 9.7 |
| CP | Ceruloplasmin | 1.16 | $2.72 \times 10^{-1}$ | 2.2 | 38.6 |
| ABCA8 | ATP-binding cassette, sub-family A (ABC1), member 8 | 1.07 | $5.38 \times 10^{-1}$ | 3.4 | 3.4 |

Any of the CSC biomarkers described herein, either taken alone or in combination (e.g., CD14 or the combination of CD14 and CD44), can be used in the assay methods also described herein for analyzing a sample suspected of containing lung cancer stem cells. Results obtained from such assay methods can be used in either clinical applications or non-clinical applications, including, but not limited to, those described herein.

(ii) Analysis of Biological Samples

Any sample that may contain cancer stem cells (for example, lung cancer stem cells, liver cancer stem cell, colon cancer stem cell, or pancreatic cancer stem cell) can be analyzed by the assay methods known in the art and/or described herein. The methods described herein involved providing a sample suspected of containing cancer stem cells. In some examples, the sample may be from an in vitro assay, for example, an in vitro cell culture for studying CSC behavior and/or mechanism. In some examples, the sample to be analyzed by the assay methods described herein can be a biological sample. As used herein, a "biological sample" refers to a composition that comprises tissue, e.g., blood, plasma or protein, from a subject. A biological sample can be an initial unprocessed sample taken from a subject or a subsequently processed sample, e.g., partially purified or preserved forms. In some embodiments, the biological sample can be a body fluid sample, for example, serum, plasma, tear, urine, or saliva samples. Alternatively, the biological sample may be a tissue sample, for example, a tissue sample obtained from a tumor site or a suspected tumor site (a tissue site suspected of containing cancer cells). In some embodiments, multiple (e.g., at least 2, 3, 4, 5, or more) biological samples may be collected from a subject, over time or at particular time intervals, for example to assess the disease progression or evaluate the efficacy of a treatment.

A biological sample can be obtained from a subject using any means known in the art. For example, the sample can be obtained from the subject by removing the sample (e.g., a tumor tissue sample) from the subject, e.g., via a surgical procedure (e.g., thoracotomy), a biopsy procedure, by needle aspiration, or by thoracentesis.

The terms "patient," "subject," or "individual" may be used interchangeably and refer to a subject who needs the analysis as described herein. In some embodiments, the subject is a human or a non-human mammal. In some embodiments, a subject is a human subject suspected of having or at risk for cancer, for example, lung cancer, colon cancer, liver cancer, or pancreatic cancer. Such a subject may exhibit one or more symptoms associated with the cancer. Alternatively or in addition, such a subject may have one or more risk factors for the cancer, for example, an environmental factor or genetic factor associated with the cancer (e.g., exposure to pollution).

Alternatively, the subject who needs the analysis described herein may be a patient having cancer, such as lung cancer, colon cancer, liver cancer, or pancreatic cancer. Such a subject may currently be having a relapse, or may have suffered from the disease in the past (e.g., currently relapse-free). In some examples, the subject is a human patient who may be on a treatment of the cancer, for example, a treatment involving surgery, chemotherapy, immunotherapy, or radiation therapy. In other instances, such a human patient may be free of such a treatment.

In some examples, the cancer is lung cancer. Examples of lung cancer include, without limitation, non-small cell lung cancer (NSCLC), adenocarcinoma, adenocarcinoma in situ (AIS), minimally invasive adenocarcinoma (MIA), squamous cell carcinoma, large cell carcinoma, large cell neuroendocrine tumors, small cell lung cancer (SCLC), mesothelioma, and carcinoid tumors.

Any of the samples described herein can be subject to analysis using the assay methods described herein, which involve measuring the level of one or more CSC biomarkers as described herein. In some examples, the biomarker is CD14 (either membrane-bound or soluble), or CD44 (either membrane-bound or soluble). In other examples, the biomarker is a combination of CD14 and CD44. Levels (e.g., the amount) of a biomarker disclosed herein, or changes in levels the biomarker, can be assessed using conventional assays or those described herein.

As used herein, the terms "measuring" or "measurement," or alternatively "detecting" or "detection," means assessing the presence, absence, quantity or amount (which can be an effective amount) of a substance within a sample, including the derivation of qualitative or quantitative concentration levels of such substances, or otherwise evaluating the values or categorization of a subject.

In some embodiments, the level of a biomarker is assessed or measured by directly detecting the protein in a sample such as a biological sample. Alternatively or in addition, the level of a protein can be assessed or measured by indirectly in a biological sample, for example, by detecting the level of activity of the protein (e.g., enzymatic assay).

The level of a protein (CD14 and/or CD44) may be measured using an immunoassay. Examples of immunoassays include, without limitation immunoblotting assay (e.g., Western blot), immunohistochemical analysis, flow cytometry assay, immunofluorescence assay (IF), enzymelinked immunosorbent assays (ELISAs) (e.g., sandwich ELISAs), radio immunoassays, electrochemiluminescence-based detection assays, magnetic immunoassays, lateral flow assays, and related techniques. Additional suitable immunoassays for detecting a biomarker provided herein will be apparent to those of skill in the art.

Such immunoassays may involve the use of an agent (e.g., an antibody) specific to the target biomarker, e.g., CD14 or CD44. A detection agent such as an antibody that "specifically binds" to a target biomarker is a term well understood in the art, and methods to determine such specific binding are also well known in the art. An antibody is said to exhibit "specific binding" if it reacts or associates more frequently, more rapidly, with greater duration and/or with greater affinity with a particular target biomarker than it does with alternative biomarkers. It is also understood by reading this definition that, for example, an antibody that specifically binds to a first target peptide may or may not specifically or preferentially bind to a second target peptide. As such, "specific binding" or "preferential binding" does not necessarily require (although it can include) exclusive binding. Generally, but not necessarily, reference to binding means preferential binding. In some examples, an antibody that "specifically binds" to a target peptide or an epitope thereof may not bind to other peptides or other epitopes in the same antigen.

As used herein, the term "antibody" refers to a protein that includes at least one immunoglobulin variable domain or immunoglobulin variable domain sequence. For example, an antibody can include a heavy (H) chain variable region (abbreviated herein as $V_H$), and a light (L) chain variable region (abbreviated herein as $V_L$). In another example, an antibody includes two heavy (H) chain variable regions and two light (L) chain variable regions. The term "antibody" encompasses antigen-binding fragments of antibodies (e.g., single chain antibodies, Fab and sFab fragments, F(ab')$_2$, Fd fragments, Fv fragments, scFv, and domain antibodies (dAb) fragments (de Wildt et al., Eur J Immunol. 1996; 26(3):629-39.)) as well as complete antibodies. An antibody can have the structural features of IgA, IgG IgE, IgD, IgM (as well as subtypes thereof). Antibodies may be from any source, but primate (human and non-human primate) and primatized are preferred.

In some embodiments, the antibodies as described herein can be conjugated to a detectable label and the binding of the detection reagent to the peptide of interest can be determined based on the intensity of the signal released from the detectable label. Alternatively, a secondary antibody specific to the detection reagent can be used. One or more antibodies may be coupled to a detectable label. Any suitable label known in the art can be used in the assay methods described herein. In some embodiments, a detectable label comprises a fluorophore. As used herein, the term "fluorophore" (also referred to as "fluorescent label" or "fluorescent dye") refers to moieties that absorb light energy at a defined excitation wavelength and emit light energy at a different wavelength. In some embodiments, a detection moiety is or comprises an enzyme. In some embodiments, an enzyme is one (e.g., β-galactosidase) that produces a colored product from a colorless substrate.

In some examples, an assay method described herein is applied to measure the level of a cell surface biomarker, for example, membrane-bound CD14 and/or CD44 on cells contained in a sample. Such cells may be collected via routine practice and the level of cell surface biomarkers can be measured via a conventional method, for example, FACS.

In other examples, an assay method described herein is applied to measure the level of a circulate biomarker (soluble biomarker), for example CD14, in a sample, which can be a blood sample or plasma sample. Any of the assays known in the art, e.g., immunoassays can be used for measuring the level of such biomarkers.

It will be apparent to those of skill in the art that this disclosure is not limited to immunoassays. Detection assays that are not based on an antibody, such as mass spectrometry, are also useful for the detection and/or quantification of lung CSC biomarkers as provided herein. Assays that rely on a chromogenic substrate can also be useful for the detection and/or quantification of lung CSC biomarkers as provided herein.

Alternatively, the level of a nucleic acid encoding a CSC biomarker in a sample can be measured via a conventional method. In some embodiments, measuring the expression level of nucleic acid encoding the CSC biomarker comprises measuring mRNA. In some embodiments, the expression level of mRNA encoding a CSC biomarker can be measured using real-time reverse transcriptase (RT) Q-PCR or a nucleic acid microarray. Methods to detect biomarker nucleic acid sequences include, but are not limited to, polymerase chain reaction (PCR), reverse transcriptase-PCR (RT-PCR), in situ PCR, quantitative PCR (Q-PCR), real-time quantitative PCR (RT Q-PCR), in situ hybridization, Southern blot, Northern blot, sequence analysis, microarray analysis, detection of a reporter gene, or other DNA/RNA hybridization platforms.

Any binding agent that specifically binds to a desired biomarker may be used in the methods and kits described herein to measure the level of a biomarker in a sample. In some embodiments, the binding agent is an antibody or an aptamer that specifically binds to a desired protein biomarker. In other embodiments, the binding agent may be one or more oligonucleotides complementary to a coding nucleic acid or a portion thereof. In some embodiments, a sample may be contacted, simultaneously or sequentially, with more than one binding agent that bind different protein biomarkers (e.g., multiplexed analysis).

To measuring the level of a target biomarker, a sample can be in contact with a binding agent (a detection agent) under suitable conditions. In general, the term "contact" refers to an exposure of the binding agent with the sample or cells collected therefrom for suitable period sufficient for the formation of complexes between the binding agent and the target biomarker in the sample, if any. In some embodiments, the contacting is performed by capillary action in which a sample is moved across a surface of the support membrane.

In some embodiments, the assays may be performed on low-throughput platforms, including single assay format. For example, a low throughput platform may be used to measure the presence and amount of a protein in biological samples (e.g., biological tissues, tissue extracts) for diagnostic methods, monitoring of disease and/or treatment progression, and/or predicting whether a disease or disorder may benefit from a particular treatment.

In some embodiments, it may be necessary to immobilize a binding agent to the support member. Methods for immobilizing a binding agent will depend on factors such as the nature of the binding agent and the material of the support member and may require particular buffers. Such methods will be evident to one of ordinary skill in the art. For example, the biomarker set in a biological sample as described herein may be measured using any of the kits and/or detecting devices which are also described herein.

The type of detection assay used for the detection and/or quantification of a cancer stem cell biomarker such as those provided herein will depend on the particular situation in which the assay is to be used (e.g., clinical or research applications), and on the kind and number of biomarkers to be detected, and/or on the kind and number of patient samples to be run in parallel.

The assay methods described herein may be used for both clinical and non-clinical purposes. Some examples are provided herein.

Diagnostic and/or Prognostic Applications

The levels of one or more of the CSC biomarkers in a biological sample derived from a subject, measured by the assay methods described herein, can be used for various clinical purposes, for example, detecting cancer cells, particularly lung cancer stem cells in a biological sample from a subject (e.g., a human patient), identifying subject as having cancer associated with poor prognosis, monitoring the progress of cancer development in a subject, assessing the efficacy of a treatment for the cancer in a subject, identifying patients suitable for a particular treatment, predicting cancer relapse in a subject, and/or adjustment treatment of the cancer based on disease development, prognosis results, and/or efficacy of current treatment. Accordingly, described herein are diagnostic and prognostic methods for cancer, for example, cancer associated with poor prognosis, based on the level of one or more CSC biomarkers described herein, e.g., CD14 or a combination of CD14 and CD44. Exemplary types of cancer include lung cancer (e.g., those described herein such as NSCLC), liver cancer, colon cancer, and pancreatic cancer.

When needed, the level of a biomarker in a sample as determined by an assay methods described herein may be normalized with an internal control in the same sample or with a standard sample (having a predetermined amount of the biomarker) to obtain a normalized value. Either the raw value or the normalized value of the biomarker can then be compared with that in a reference sample or a control sample. An elevated value of the biomarker in a sample obtained from a subject as relative to the value of the same biomarker in the reference or control sample is indicative of presence of CSCs in the sample. A subject carrying CSCs indicates that the subject may have a target cancer as described herein, e.g., cancer associated with poor prognosis or at risk for cancer development.

In some embodiments, the level of the biomarker in a sample obtained from a subject can be compared to a predetermined threshold for that biomarker, an elevation from which may indicate the subject carry CSCs and thus may have a target cancer, e.g., a target cancer associated with poor prognosis or at risk for cancer development and/or metastasis.

The control sample or reference sample may be a biological sample obtained from a healthy individual, who may be of the same ethnic group, age, and/or gender as the subject from whom a sample is obtained for analysis. Alternatively, the control sample or reference sample contains a known amount of the biomarker to be assessed. In some embodiments, the control sample or reference samples is a biological sample obtained from a control subject.

As used herein, a control subject may be a healthy individual, i.e., an individual that is apparently free of a target cancer (e.g., lung cancer such as NSCLC, liver cancer, colon cancer, or pancreatic cancer) at the time the level of the protein(s) is measured or has no history of the disease. A control subject may also represent a population of healthy subjects, who preferably would have matches features (e.g., age, gender, ethnic group) as the subject being analyzed by an assay method described herein.

The control level can be a predetermined level or threshold. Such a predetermined level can represent the level of the protein in a population of subjects that do not have or are not at risk for the target disease (e.g., the average level in the population of healthy subjects). It can also represent the level of the protein in a population of subjects that have the target disease.

The predetermined level can take a variety of forms. For example, it can be single cut-off value, such as a median or mean. In some embodiments, such a predetermined level can be established based upon comparative groups, such as where one defined group is known to have a target cancer and another defined group is known to not have the target cancer. Alternatively, the predetermined level can be a range, for example, a range representing the levels of the protein in a control population.

In some examples, the predetermined level can be a median risk score in association with a target cancer as described herein. A median risk score is a well-known reference points for distinguishing a high risk population from a low risk population as indicated by the level of one or more biomarkers, which, in turn, is indicative of high risk versus low risk of a particular condition (e.g., cancer occurrence, cancer prognosis, or treat efficacy). See, e.g., Chen et al., *N. Engl. J. Med.* 356(1):11-20 (2007). It can be used as the cut-off value in the diagnostic/prognostic methods as described herein. In some instances, a median risk score can be determined as follows. The levels of a biomarker can be determined in healthy patients (patients free of a target disease) and in patients having the target disease (e.g., cancer such as those described herein). The frequency distribution of the level of the biomarker in the tested patients can be plotted to determine a risk score for each patient, which is representative of the risk profile for the tested patients in connection with the target disease. The risk score is then used to classify patients into high-risk or low-risk group. To avoid the effect of extreme values and set the number of patients in the two groups (high vs. low risk group) equal in the training dataset, the $50^{th}$ percentile (the median risk score) can be used as the cut-off value, which can be the predetermined value used in the methods described herein.

The control level as described herein can be determined by routine technology. In some examples, the control level can be obtained by performing a conventional method (e.g., the same assay for obtaining the level of the protein a test sample as described herein) on a control sample as also described herein. In other examples, levels of the protein can be obtained from members of a control population and the results can be analyzed by, e.g., a computational program, to obtain the control level (a predetermined level) that represents the level of the protein in the control population.

By comparing the level of a biomarker in a sample obtained from a candidate subject to the reference value as described herein, it can be determined as to whether the candidate subject has or is at risk for a target cancer associated with poor prognosis. For example, if the level of biomarker(s) in a sample of the candidate subject increased as compared to the reference value, the candidate subject might be identified as having or at risk for the target cancer associated with poor prognosis. When the reference value represents the value range of the level of the biomarker in a population of subjects that carry cancer stem cells and/or have the cancer associated with poor prognosis, the value of biomarker in a sample of a candidate falling in the range indicates that the candidate subject has or is at risk for the target cancer associated with poor prognosis.

As used herein, "an elevated level" or "a level above a reference value" means that the level of the biomarker is higher than a reference value, such as a pre-determined threshold of a level the biomarker in a control sample. Control levels are described in detail herein. An elevated level of a biomarker includes a level of the biomarker that is, for example, 1%, 5%, 10%, 20%, 30%, 40%, 50%, 60%, 70%, 80%, 90%, 100%, 150%, 200%, 300%, 400%, 500% or more above a reference value. In some embodiments, the level of the biomarker in the test sample is at least 1.1., 1.2, 1.3, 1.4, 15, 1.6, 1.7, 1.8, 1.9, 2, 2.5, 3, 3.5, 4, 4.5, 5, 5, 6, 7, 8, 9, 10, 50, 100, 150, 200, 300, 400, 500, 1000, 10000-fold or 5 more higher than the level of the biomarker in a reference sample.

In some examples, the biomarker comprises CD14. The presence of CD14 (membrane-bound and/or soluble CD14) in a sample obtained from a candidate subject such as a human patient or an elevated level of CD14 in such a sample as relative to a sample of the same type from a control subject would be indicative of presence of cancer stem cells in the candidate subject, which in turn, would be indicative of poor cancer prognosis.

In some examples, the biomarker may further comprise CD44. A high expression level of CD44 in the sample obtained from the candidate subject, optionally in combination with an elevated level of CD14 as described herein, would be indicative of presence of cancer stem cells in the candidate subject, which in turn, would be indicative of poor cancer prognosis. In some instances, a high expression level of CD44 refers to an expression level that is higher than a predetermined level, for example, no less than the median risk score of the corresponding target cancer.

In some embodiments, the candidate subject is a human patient having a symptom of a target cancer (e.g., lung cancer such as NSCLC, liver cancer, colon cancer, or pancreatic cancer). For example, the subject has fatigue, cough, shortness of breath, chest pain, loss of appetite, weight loss, hoarseness, coughing up of blood, chronic bronchitis, chronic pneumonia, wheezing, or a combination thereof. In other embodiments, the subject has no symptom of a target cancer at the time the sample is collected, has no history of a symptom of the target cancer, or no history of the target cancer. In yet other embodiments, the subject is resistant to a chemotherapy, a radiation therapy, immunotherapy, or a combination thereof.

A subject identified in the methods described herein as carrying cancer stem cells of the target cancer or have the target cancer (e.g., lung cancer associated with poor prognosis) may be subject to a suitable treatment, such as treatment with a chemotherapy, as described herein.

The assay methods and kits described herein also can be applied for evaluation of the efficacy of a treatment for a target cancer such as those described herein, given the correlation between the level of the biomarkers and such cancers. For examples, multiple biological samples (e.g., tissue samples or body fluid samples) can be collected from a subject to whom a treatment is performed either before and after the treatment or during the course of the treatment. The levels of a biomarker can be measured by any of the assay methods as described herein and values (e.g., amounts) of a biomarker can be determined accordingly. For example, if an elevated level of a biomarker indicates that a subject has a lung cancer and the level of the biomarker decreases after the treatment or over the course of the treatment (the level of the biomarker in a later collected sample as compared to that in an earlier collected sample), it indicates that the treatment is effective. In some examples, the treatment involves an effective amount of a therapeutic agent, such as a chemotherapeutic agent. Examples of the chemotherapeutic agents include, but are not limited to, carboplatin (Paraplatin) or cisplatin (Platinol), docetaxel (Docefrez, Taxotere), gemcitabine (Gemzar), nab-paclitaxel (Abraxane), paclitaxel (Taxol), pemetrexed (Alimta), and vinorelbine (Navelbine).

If the subject is identified as not responsive to the treatment, a higher dose and/or frequency of dosage of the therapeutic agent are administered to the subject identified. In some embodiments, the dosage or frequency of dosage of the therapeutic agent is maintained, lowered, or ceased in a subject identified as responsive to the treatment or not in need of further treatment. Alternatively, a different treatment can be applied to the subject who is found as not responsive to the first treatment.

In other embodiments, the values of a biomarker or biomarker set can also be relied on to identify a target cancer as those described herein that may be treatable, for example by a chemotherapeutic agent. To practice this method, the level of a biomarker in a sample (e.g., a tissue sample or a body fluid sample) collected from a subject having a target cancer can be measured by a suitable method, e.g., those described herein such as a Western blot or a RT Q-PCR assay. If the level of the biomarker is elevated from the reference value, it indicates that a chemotherapeutic agent may be effective in treating the disease. If the disease is identified as being susceptible (can be treated by) to a chemotherapeutic agent, the method can further comprise administering to the subject having the disease an effective amount of a chemotherapeutic agent, such as carboplatin (Paraplatin) or cisplatin (Platinol), docetaxel (Docefrez, Taxotere), gemcitabine (Gemzar), nab-paclitaxel (Abraxane), paclitaxel (Taxol), pemetrexed (Alimta), and vinorelbine (Navelbine).

Also within the scope of the present disclosure are methods of evaluating the severity of a target cancer as those described herein. For example, as described herein, a target cancer may be in the quiescent state (remission), during which the subject does not experience symptoms of the disease. For example, a lung cancer relapses are typically recurrent episodes in which the subject may experience a symptom of a lung cancer including, but not limited to, fatigue, cough, shortness of breath, chest pain, loss of appetite, weight loss, hoarseness, coughing up of blood, chronic bronchitis, chronic pneumonia, wheezing, or a combination thereof. In some embodiments, the level of one or more biomarkers is indicative of whether the subject will experience, is experiencing, or will soon experience relapse of a target cancer (e.g., lung cancer relapse). In some embodiments, the methods involve comparing the level of a biomarker in a sample obtained from a subjecting having a target cancer to the level of the biomarker in a sample from the same subject, for example a sample obtained from the same subject at remission or a sample obtained from the same subject during a relapse.

Non-Clinical Applications

Further, levels of any of the CSC biomarkers described herein may be applied for non-clinical uses, for example, for research purposes. In some embodiments, the methods described herein may be used to study the behavior of cancer stem cells and/or mechanisms (e.g., the discovery of novel biological pathways or processes involved cancer stem cells in cancer development and/or metastasis).

In some embodiments, the levels of biomarker sets, as described herein, may be relied on in the development of new therapeutics for a lung cancer. For example, the levels of a biomarker may be measured in samples obtained from a subject having been administered a new therapy (e.g., a clinical trial). In some embodiments, the level of the biomarker set may indicate the efficacy of the new therapeutic or the progression of the cancer in the subject prior to, during, or after the new therapy.

Further, one or more of the CSC biomarkers described herein may be used for enriching cancer stem cells, which can be used for various purposes, including studies on cancer biology and development of new anti-cancer agents that specifically target cancer stem cells. As used herein, the term "enriching lung cancer stem cells," means isolating or separating lung cancer stem cells from a biological sample such that the lung cancer stem cells are sufficiently free of other materials present in the biological sample. In some embodiments, enriching lung cancer stem cells comprises separating lung cancer stem cells from non-stem cells.

Kits and Detecting Devices for Measuring Protein Biomarkers

The present disclosure also provides kits and detecting devices for use in measuring the level of one or more biomarkers as described herein. Such a kit or detecting device can comprise one or more binding agents that specifically bind to the target biomarkers, such as those listed in Table 1. For example, such a kit or detecting device may comprise at least one binding agent that is specific to one protein biomarkers selected from Table 1. In some instances, the kit or detecting device comprises binding agents specific to two or more members of the protein biomarker set described herein.

In some embodiments, one or more of the binding agents (e.g., detection agents) can be an antibody that specifically binds to a protein of the biomarker set. In some embodiments, the one or more binding agents is an aptamer, such as a peptide aptamer or oligonucleotide aptamer, that specifically binds to a protein of the biomarker set.

In some embodiments, the kits further comprise a detection agent (e.g., an antibody binding to the binding agent) for detecting binding of the agent to the protein(s) of the biomarker set. The detection agent can be conjugated to a label. In some embodiments, the detection agent is an antibody that specifically binds to at least one of the binding agents. In some embodiments, the binding agent comprises a tag that can be identified and, directly or indirectly, bound by a detection agent.

In the kit or detecting device, one or more of the binding agents may be immobilized on a support member, e.g., a membrane, a bead, a slide, or a multi-well plate. Selection of an appropriate support member for the assay will depend on various factor such as the number of samples and method of detecting the signal released from label conjugated to the agent.

In some embodiments, the support member is a membrane, such as a nitrocellulose membrane, a polyvinylidene fluoride (PVDF) membrane, or a cellulose acetate membrane. In some examples, the assay may be in a Western blot assay format or a nucleic acid microarray assay format.

In some embodiments, the support member is a multi-well plate, such as an ELISA plate. In some embodiments, the immunoassays described herein can be carried out on high throughput platforms. In some embodiments, multi-well plates, e.g., 24-, 48-, 96-, 384- or greater well plates, may be used for high throughput immunoassays. Individual immunoassays can be carried out in each well in parallel. Therefore, it is generally desirable to use a plate reader to measure multiple wells in parallel to increase assay throughput. In some embodiments, plate readers that are capable of imaging multi-wells (e.g., 4, 16, 24, 48, 96, 384, or greater wells) in parallel can be used for this platform. For example, a commercially available plate reader (e.g., the plate vision system available from Perkin Elmer, Waltham, MA) may be used. This plate reader is capable of kinetic-based fluorescence analysis. The plate vision system has high collection efficiency optics and has special optics designed for the analysis of 96 wells in parallel. Additional suitable parallel plate readers include but are not limited to the SAFIRE (Tecan, San Jose, CA), the FLIPRTETRA® (Molecular Devices, Union City, CA), the FDS S7000 (Hamamatsu, Bridgewater, NJ), and the CellLux (Perkin Elmer, Waltham, MA).

The kit can also comprise one or more buffers as described herein but not limited to a coating buffer, a blocking buffer, a wash buffer, and/or a stopping buffer.

In some embodiments, the kit can comprise instructions for use in accordance with any of the methods described herein. The included instructions can comprise a description of how to use the components contained in the kit for measuring the level of a biomarker set (e.g., protein or nucleic acid) in a biological sample collected from a subject, such as a human patient.

The instructions relating to the use of the kit generally include information as to the amount of each component and suitable conditions for performing the assay methods described herein. The components in the kits may be in unit doses, bulk packages (e.g., multi-dose packages), or sub-unit doses. Instructions supplied in the kits of the present disclosure are typically written instructions on a label or package insert (e.g., a paper sheet included in the kit), but machine-readable instructions (e.g., instructions carried on a magnetic or optical storage disk) are also acceptable.

The label or package insert indicates that the kit is used for evaluating the level of a biomarker set. Instructions may be provided for practicing any of the methods described herein.

The kits of this present disclosure are in suitable packaging. Suitable packaging includes, but is not limited to, vials, bottles, jars, flexible packaging (e.g., sealed Mylar or plastic bags), and the like. Also contemplated are packages for use in combination with a specific device, such as a PCR machine, a nucleic acid array, or a flow cytometry system.

Kits may optionally provide additional components such as interpretive information, such as a control and/or standard or reference sample. Normally, the kit comprises a container and a label or package insert(s) on or associated with the container. In some embodiments, the present disclosure provides articles of manufacture comprising contents of the kits described above.

Treatment of Cancer

A subject at risk for or suffering from a target cancer as described herein (e.g., lung cancer, liver cancer, colon cancer, or pancreatic cancer, which may be associated with poor prognosis), as identified using the methods described herein, may be treated with any appropriate therapeutic agent. In some embodiments, provided methods include selecting a treatment for a subject based on the output of the described method, e.g., measuring the level of a biomarker set.

In some embodiments, the method comprises one or both of selecting or administering a therapeutic agent, e.g., a chemotherapy, a radiation therapy, a surgical therapy and/or an immunotherapy, for administration to the subject based on the output of the assay, e.g., biomarker detection.

In some embodiments, the therapeutic agent is administered one or more times to the subject. The therapeutic agent, e.g., chemotherapy, radiation therapy, surgical therapy and/or immunotherapy, may be administered along with another therapy as part of a combination therapy for treatment of the lung cancer. Combination therapy, e.g., chemotherapy and radiation therapy, may be provided in multiple different configurations. The first therapy may be administered before or after the administration of the other therapy. In some situations, the first therapy and another therapy (e.g., a therapeutic agent) are administered concurrently, or in close temporal proximity (e.g., a short time interval between the therapies, such as during the same treatment session). The first agent and the other therapy may also be administered at greater temporal intervals.

In some embodiments, a chemotherapeutic agent is administered to a subject. Examples of the chemotherapeutic agents include, but are not limited to, Carboplatin or Cisplatin, Docetaxel, Gemcitabine, Nab-Paclitaxel, Paclitaxel, Pemetrexed, and Vinorelbine.

In some embodiments, a radiation therapy is administered to a subject. Examples of radiation therapy include, but are not limited to, ionizing radiation, gamma-radiation, neutron beam radiotherapy, electron beam radiotherapy, proton therapy, brachytherapy, systemic radioactive isotopes and radiosensitizers.

In some embodiments, a surgical therapy is administered to a subject. Examples of a surgical therapy include, but are not limited to, a lobectomy, a wedge resection, a segmentectomy, and a pneumonectomy.

In some embodiments, an immunotherapeutic agent is administered to a subject. In some embodiments, the immunotherapeutic agent is a PD-1 inhibitor or a PD-L1 inhibitor.

In some embodiments, the immunotherapeutic agent is Nivolumab. In some embodiments, the immunotherapeutic agent is Pembrolizumab.

Additional examples of chemotherapy include, but are not limited to, Platinating agents, such as Carboplatin, Oxaliplatin, Cisplatin, Nedaplatin, Satraplatin, Lobaplatin, Triplatin, Tetranitrate, Picoplatin, Prolindac, Aroplatin and other derivatives; Topoisomerase I inhibitors, such as Camptothecin, Topotecan, irinotecan/SN38, rubitecan, Belotecan, and other derivatives; Topoisomerase II inhibitors, such as Etoposide (VP-16), Daunorubicin, a doxorubicin agent (e.g., doxorubicin, doxorubicin HC1, doxorubicin analogs, or doxorubicin and salts or analogs thereof in liposomes), Mitoxantrone, Aclarubicin, Epirubicin, Idarubicin, Amrubicin, Amsacrine, Pirarubicin, Valrubicin, Zorubicin, Teniposide and other derivatives; Antimetabolites, such as Folic family (Methotrexate, Pemetrexed, Raltitrexed, Aminopterin, and relatives); Purine antagonists (Thioguanine, Fludarabine, Cladribine, 6-Mercaptopurine, Pentostatin, clofarabine and relatives) and Pyrimidine antagonists (Cytarabine, Floxuridine, Azacitidine, Tegafur, Carmofur, Capacitabine, Gemcitabine, hydroxyurea, 5-Fluorouracil (5FU), and relatives); Alkylating agents, such as Nitrogen mustards (e.g., Cyclophosphamide, Melphalan, Chlorambucil, mechlorethamine, Ifosfamide, mechlorethamine, Trofosfamide, Prednimustine, Bendamustine, Uramustine, Estramustine, and relatives); nitrosoureas (e.g., Carmustine, Lomustine, Semustine, Fotemustine, Nimustine, Ranimustine, Streptozocin, and relatives); Triazenes (e.g., Dacarbazine, Altretamine, Temozolomide, and relatives); Alkyl sulphonates (e.g., Busulfan, Mannosulfan, Treosulfan, and relatives); Procarbazine; Mitobronitol, and Aziridines (e.g., Carboquone, Triaziquone, ThioTEPA, triethylenemalamine, and relatives); Antibiotics, such as Hydroxyurea, Anthracyclines (e.g., doxorubicin agent, daunorubicin, epirubicin and other derivatives); Anthracenediones (e.g., Mitoxantrone and relatives); Streptomyces family (e.g., Bleomycin, Mitomycin C, Actinomycin, Plicamycin); and Ultraviolet light.

Without further elaboration, it is believed that one skilled in the art can, based on the above description, utilize the present disclosure to its fullest extent. The following specific embodiments are, therefore, to be construed as merely illustrative, and not limitative of the remainder of the disclosure in any way whatsoever. All publications cited herein are incorporated by reference for the purposes or subject matter referenced herein.

EXAMPLES

Example 1

Identification of Proteins Differentially Present on Lung Cancer Stem Cells (CSCs) as Compared to Primary Lung Cancer Cells Materials and Methods
Lung Cancer Cell Lines The human NSCLC cell lines NCI-A549, EKVX, PC9 and HCC827 were obtained from the National Cancer Institute (National Institutes of Health, Bethesda, MD, USA) or the American Type Culture Collection (ATCC, Manassas, VA, USA). Human lung cancer cell lines (CLS1, CL100, CL141 and CL152) were established using primary cultures from lung cancer patients. The cells were cultured in RPMI 1640 medium supplemented with 10% FBS at 37° C. under a humidified atmosphere consisting of 20% O2 and 5% CO2.

Co-Culture System for Culturing Lung CSCs and CAFs

Human lung CSCs and CAFs were established from freshly resected lung tumor tissues from lung cancer patients. Tumors and paired normal tissues were harvested within 30 min after resection to isolate primary lung CSC, CAF and NF cultures using a modified protocol. Lung CSCs were isolated from cancer-associated regions of resected tissues from NSCLC patients and were cultured and maintained with feeder cells, i.e., stromal fibroblasts. The samples were procured and utilized according to approved IRB protocols for research on human subjects. Written informed consent was obtained from all patients. Non-cancer associated stromal was sampled by a pathologist at least 5 cm away from neoplastic lesions (under sterile conditions) within 30 min after resection, as determined by gross examination at the time of surgical excision and subsequent histological analysis.

The tissues were processed based on a previously described protocol with modifications. In brief, the tissues were minced and incubated for 6-12 h in the presence of deoxyribonuclease 1 (1 mg/ml; Bioshop) and protease (1 mg/ml; Sigma) in S-MEM medium (GIBCO) at 4° C. After digestion, cell clumps were sieved through a 40-μm cell strainer (Falcon) to obtain single-cell suspensions. The collected cells were cultured at different cell densities ($5 \times 10^5$) in a 24-well plate with the modified culture conditions in RPMI1640 with 10% FBS at 37° C. in a humidified atmosphere containing 20% $O_2$ and 5% $CO_2$. After 30 days of culture, sphere-like colonies could be identified with the surrounding stroma cells. Sub-culturing of sphere-like cells was performed as previously described with some modifications. The spheres were collected through gentle centrifugation (58 g) after 7-10 days and dissociated enzymatically (10 min in 0.05% trypsin, 0.53 mM EDTA 4Na; Invitrogen) and mechanically using a fire-polished Pasteur pipette. The cells obtained from dissociation were passaged through a 40-μm sieve and analyzed microscopically for single-cell status. The cells, at a density of 5,000 viable cells/ml, were plated in plates pre-seeded with stromal cells as feeders ($5 \times 10^5$ cells/well). For the single cell/well clone experiments, the cells were plated in 96-well plates using a cell sorter during FACS (FACS Ariel), and the wells had been pre-seeded with feeder cells (2,000 cells/well). Sub-culturing of lung CSCs was performed as previously described with some modifications. Briefly, spheres were collected through gentle centrifugation (800 rpm), enzymatic digestion (10 min with 0.25% trypsin, 1 mM EDTA; Invitrogen) and mechanic disruption. The lung CSCs obtained from this dissociation were passaged through a 100-μm strainer, and the sieved cells were analyzed microscopically. The single cells, at a density of 5,000 viable cells/ml, were plated on 10-cm dishes pre-seeded with CAF feeder cells ($5 \times 10^5$ cells/well).

Image-Based High-Content Assay

Lung CSCs or cancer cells (200 cells/well) were added to 96-well plates pre-seeded with CAFs (2,000 cells/well) and allowed to attach to the plates overnight. After different treatments, the cells were processed following the immunofluorescence protocol with the Nanog (ReproCELL; 1:300) primary antibody (as the cancer stem-cell marker) and the mouse anti-human CD90 FITC-conjugated (5E10; BD Pharmingen; 1:100) antibody (as the CAF marker) overnight at 4° C. Next, the primary antibodies were incubated with the TRITC-conjugated secondary antibody [goat anti-rabbit IgG (H+L) Conjugate, Invitrogen] for 2 h at room temperature. The nuclei were counterstained with Hoechst 33342 dye (Invitrogen). To determine the background fluorescence level of the secondary antibody, each plate included control wells containing only the secondary antibody (stained with the Hoechst 33342 dye).

Images of the stained cells were acquired using the automated fluorescence microscopy platform.

Image Acquisition and Analysis

The stained cells were imaged using the high-content analysis platform with a 4× objective. Twelve fields per well for each wavelength were captured and montaged for further image analysis. The images were analyzed using the MetaXpress® software (Molecular Devices). First, the cancer cell nuclei (cells without FITC staining, CD90-) were identified using Multi-Wavelength Cell Scoring. The segmented cancer cell nuclei were dilated and smoothed using Morphology Filters to create a cell cluster mask. TexRed-stained positive cells were determined as Nanog-positive cells.

Real-Time Reverse Transcriptase (RT) Q-PCR

The expression level of stemness-related genes and validation of the Affymetrix microarray data for CLS1/CAF and CLS1 were performed through RT Q-PCR using an ABI Prism 7900 Sequencer (Applied Biosystems). The primers were designed using Primer Express 3.0 (Applied Biosystems) (Table 2). β-actin were used as internal controls. The expression levels were normalized to β-actin and defined as $-\Delta CT=[CT_{target}-CT_{\beta\text{-actin}}]$. The relative expression ratio was calculated as the fold change relative to the control ($2^{-\Delta\Delta CT}$). The experiments were performed in triplicate.

entiation medium for either 0, 7, or 14 days during the course of differentiation. Real-time RT-PCR was performed on these samples as described herein for peroxisome proliferator-activated receptor-gamma (PPAR-γ) and lipoprotein lipase (LPL).

Osteoblast Differentiation

To test whether cancer stem cells could differentiate into an osteogenic lineage, the CLS1 cell co-cultured with CAFs, and mesenchymal stem cells as a positive control, were analyzed following the protocol of the Osteogenesis Assay (Millipore, Cat. #SCR028) using basic growth medium supplemented with 0.1 µM dexamethasone, 0.2 mM ascorbic acid 2-phosphate and 10 mM glycerol 2-phosphate for 14 days. In brief, cells were seeded in the vitronectin/collagen coated 24-well culture plate at a density of $6\times10^4$ cells/well in RPMI medium with 10% FBS, 100 U/ml penicillin, and 100 µl streptomycin. The medium was replaced every 3 days. After 14 days, the cells were washed twice with PBS and fixed in iced cold 70% ethanol for 1 hour at room temperature. Calcium deposition was analyzed by staining with alizarin red S (Millipore, Cat. #2003999) for 30 minutes at room temperature. For the gene expression analysis during osteoblast differentiation, total mRNA was collected from cells which were grown in osteoblast differentiation medium for either 0, 3, or 7 days during the course of differentiation. Real-time RT-PCR was performed on these samples for AP and osteocalcin (OC).

TABLE 2

Primer list for Q-PCR

| Gene Symbol | UniGene ID | Forward primer | Reverse primer |
|---|---|---|---|
| Oct3/4 | Hs.249184 | TTCAGCCAAACGACCATCTG (SEQ ID NO: 1) | GAACCACACTCGGACCACATC (SEQ ID NO: 2) |
| Nanog | Hs.661360 | CACCAGTCCCAAAGGCAAAC (SEQ ID NO: 3) | GCCTTCTGCGTCACACCATT (SEQ ID NO: 4) |
| CD14 | Hs.163867 | CACAGAGGAGGGAACTGAATGAC (SEQ ID NO: 5) | AACTCTTCGGCTGCCTCTGA (SEQ ID NO: 6) |
| CD44 | Hs.502328 | TGGACACTCACATGGGAGTCAAGA (SEQ ID NO: 7) | CGACTGTTGACTGCAATGCA (SEQ ID NO: 8) |
| ACTB | Hs.520640 | CTGGAACGGTGAAGGTGACA (SEQ ID NO: 9) | CGGCCACATTGTGAACTTTG (SEQ ID NO: 10) |

Adipocyte Differentiation

To test whether cancer stem cells could differentiate into an adipogenic lineage, the CLS1 cell co-cultured with CAFs, and mesenchymal stem cells as a positive control, were examined following the protocol of the Adipogenesis Assay (Millipore, Cat. #SCR020). In brief, cells were seeded in a 24-well plate at a density of $6\times10^4$ cells/well in RPMI medium with 10% FBS, 100 U/ml penicillin, and 100 µg/ml streptomycin. After reaching confluence, cells for adipogenesis were cultured in adipogenic induction medium (Millipore, Cat. #SCR020) consisting of basic growth medium supplemented with 1 µM dexamethasone, 10 µg/ml insulin, 100 µM indomethacin, and 0.5 mM isobutylmethylxanthine (IBMX) for 21 days. The medium was replaced every 3 days. After 21 days of culture, the formation of adipocytes was evaluated fixing cells with 4% PFA and staining with oil red Odye for 50 minutes at RT. Photographs were taken by using a Axiovert 200 microscope. For the gene expression analysis during adipocyte differentiation, total mRNA was collected from cells which were grown in adipocyte differ- Membrane Proteomic Profiling Membrane protein samples were extracted from CLS1 cells co-cultured with or without CAFs and samples subjected to spiking of the internal standard, gel-assisted digestion, and triplicate LC-MS/MS analysis. The label-free quantitation across triplicate LC-MS/MS runs from cell lines were performed by IDEAL-Q software that was developed by Dr. Yu-Ju Chen's laboratory at the Institute of Chemistry, Academia Sinica. The ratios of peptides were determined by the weighted average of the normalized peptides ratios.

Gene Expression Profiling

The gene expression profiling map of CLS1/CAF and CLS1 was obtained using the AffymetrixGeneChip system (Affymetrix, Inc., Santa Clara, CA, USA) according to the manufacturer's protocol. Gene expression profiling was performed using the AffymetrixGeneChip system (Affymetrix, Inc., Santa Clara, CA, USA) according to the manufacturer's protocol.

The array data were processed by the National Taiwan University Microarray Core Facility for Genomic Medicine.

Briefly, total RNA isolated from CAFs, lung CSCs and cancer cells was used to generate cDNA (SuperscriptChoice System, Gibco BRL Life Technologies) with T7-(dT)$_{24}$ primers. Biotin-labeledribonucleotides were synthesized using a BioArray high-yield RNA transcript labeling kit (EnzoDiagnostic, Inc.) and hybridized onto the human Genome U133 Plus 2.0 chip (Affymetrix).

Results

Lung CSCs Maintain Cancer Stemness and High Tumorigenicity When Co-Cultured with CAF Feeder Cells A persistent CSCs/CAFs co-culture platform was used for identification of proteins differentially present in lung cancer stem cells (CSCs) compared to primary lung cancer cells. CAF-co-cultured CLS1 cells (CLS1/CAF) maintained a high population of Nanog$^+$ cells (FIG. 1, panel A), a capacity to differentiate into adipocytes and osteoblasts (FIG. 1, panels B and C), and an ability to generate tumors in mouse xenografts when injected at low cell numbers (<100 cells) (FIG. 1, panel D). However, when CAFs were removed during passaging, such cancer stemness characteristics were lost, observed by a decrease in the Nanog positive population (FIG. 1, panel A) as well as a reduction in tumor initiating frequency from 1/11 to 1/1774 (FIG. 1, panel D). Accordingly, the CSCs/CAFs co-culture model provides a platform for culturing cancer stem cells and maintaining cancer cell stemness.

High-Levels of CD14 and CD44 are Present on CSCs as Compared to Primary Lung Cancer Cells To identify cell surface protein of CSCs to interact with surrounding CAFs, we performed transcriptomic and membrane proteomic profiling of CSCs/CAFs and differentiated cancer cells followed by CSC markers screening strategy (FIG. 1, panel E). The analysis demonstrated that CD14 and CD44 cell surface proteins were up-regulated in CSCs/CAFs compared to differentiated cancer cells. Subsequent analyses were focused on CD14 and CD44 proteins that were at the top of the profiling data (Table 1 above).

To investigate the candidate CSC markers, CD14 and CD44 expression was correlated with the clinical hazard ratio of 152 stage I lung cancer patients from a published Japan cohort. These results indicated that patients with high-level expression of CD14 in tumor cells demonstrated significantly poorer relapse-free survival compared to patients with low-level expression of CD14 (P<0.05, Kaplan-Meier analysis; FIG. 1, panel F). Analysis of CD14 and CD44 on patient prognoses revealed that patients with high-level expression of CD14 and CD44 in tumor cells demonstrated worse relapse-free survival compared to those with low-level expression of CD14 and CD44 in tumor cells (CD14+CD44, P<0.05, Kaplan-Meier analysis; FIG. 1, panel F).

Example 2

CD14 and CD44 Correlated with Poor Prognosis

Materials and Methods

Patients and Tumor Specimens

Lung tumor tissue specimens were obtained from patients (N=80) with histologically confirmed NSCLC who had undergone complete surgical resections at the National Taiwan University Hospital (Taipei, Taiwan) between Dec. 28, 1995 and Dec. 26, 2005. This investigation was approved by the Institutional Review Board of the National Taiwan University Hospital (201103028RC). The enrolled patients were classified as stage I, and they had not been previously treated with neoadjuvant chemotherapy or irradiation therapy. All patients provided informed consent. All specimens were formalin-fixed, sectioned, stained with H&E and examined through microscopy. Pathological staging was performed by Dr. Yih-Leong Chang according to the international staging system for lung cancer.

Immunohistochemistry Analysis Tumor Samples from Lung Cancer Patients.

The immunohistochemistry analysis of tumor samples was performed according to standard procedures and modified as described herein. Dual immunohistochemical stains for CD14 (clone EPR3653; Epitomics; dilution 1:400) and CD44 (clone DF1485; BioGenex; dilution 1:200) were performed. After deparaffinization and rehydration, 5 μm thick sections for heat-mediated antigen retrieval was performed with 1 mM Tris-EDTA buffer, 10 minutes each. After blocking with hydrogen peroxide and Ultra V Block, the specimens were incubated at room temperature for 2 hours with the primary antibody. Washing steps were performed with TBST buffer (Tris buffer [TBS: 50 mM, pH 7.6] plus 0.1% Tween 20). Dual staining was conducted with the multivision polymer detection system (Thermo scientific; TL-012-MARH) by using HRP-conjugated polymer for the rabbit anti-human antibody (CD14) and alkaline phosphatase-conjugated polymer for the mouse anti-human antibody (CD44). The sections used for IHC analysis of Nanog protein expression were first autoclaved in Antigen Retrieval AR-10 Solution (Biogenex) or Antigen Retrieval Citra Solution (Biogenex) at 121° C. for 10 min. The samples were then treated with 3% $H_2O_2$-methanol and sequentially subjected to incubation with Ultra V Block (Lab Vision Corporation) for 10 min and incubation with a rabbit monoclonal anti-Nanog (D73G4, Cell signaling; 1:300) for 2 h at room temperature. Detection of the immunostaining was performed using the Super Sensitive Non-Biotin Polymer HRP Detection System (BioGenex), according to the manufacturer's instructions.

Results

Figure 2:
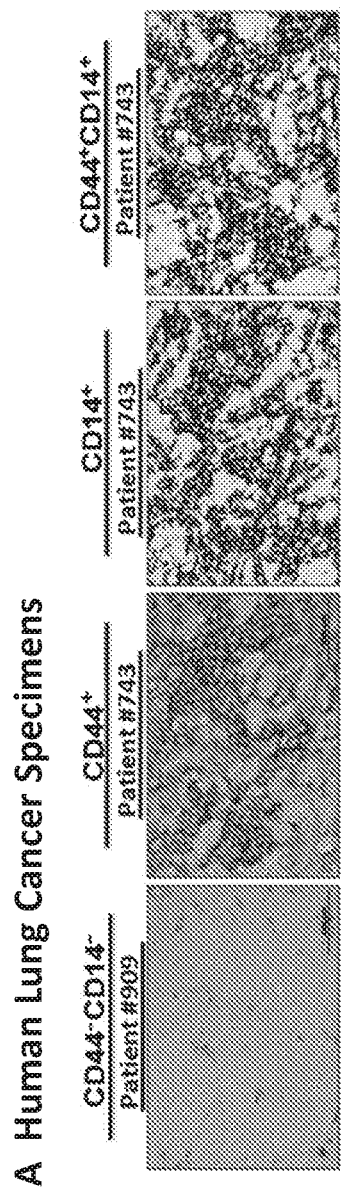
FIG. 2 shows the clinical significance of CD44 and CD14 in cancer cells for Stage I NSCLC patients. A:IHC staining of CD44 and CD14 in cancer cells from serial dissections of primary tumor specimens obtained from a clinical cohort of 80 patients with stage I NSCLC who underwent surgical resections. The images were obtained from different patients with low (score<median risk score) and high (score ≥median risk score) expression of CD44 in cancer cells (original magnification, 100×). Otherwise, the images were obtained from different patients with negative (score=0) and positive (score>0) group of CD14 in cancer cells (original magnification, 100×). B and C:The patients were designated as having high or low CD44 expression (cut-off value=median risk score); negative and positive CD14 expression. The results showed a significant difference in the Kaplan-Meier estimates of overall (Panel B) and relapse-free (Panel C) survival between the high and low expression groups. P values were obtained from two-sided log-rank tests. By combining the expression levels of CD44 and CD14 in cancer cells, the patients were divided into three groups: a high CD44/positive CD14 group, a low CD44/negative CD14 and others. The results showed a significant difference in Kaplan-Meier estimates of overall and relapse-free survival. P values were obtained from 2-sided log-rank tests.
Figure 2:
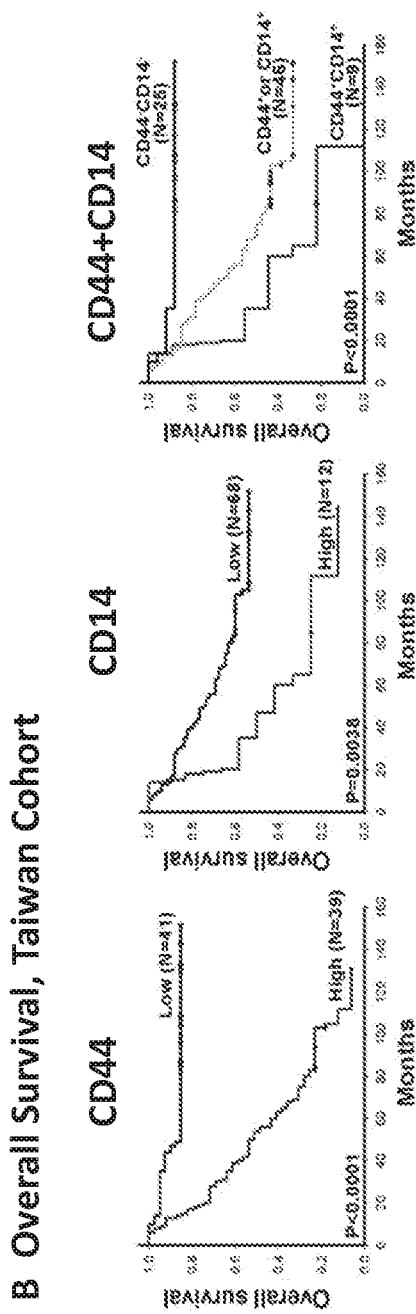
Figure 2:
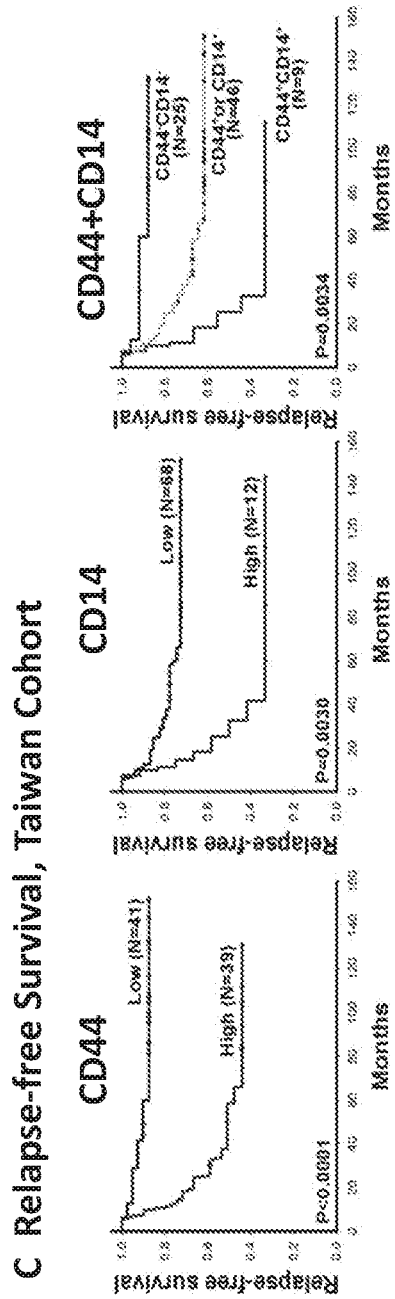

To determine the clinical relevance and importance of CD14 and CD44 in the early stages of tumorigenesis, tumor specimens from 80 patents with stage I NSCLC were collected, and sections of each specimen were stained with antibodies against CD14 and CD44 via immunohistochemical analysis. Representative tissue sections are shown in FIG. 2, panel A. The clinical characteristics of these patients are provided in Tables 3 and 4.

TABLE 3

Clinical Characteristics of CD14 and CD44 Expression in Lung Cancer Patients

|  | High (%) | Low (%) | p-value |
|---|---|---|---|
| CD14 | N = 12 | N = 68 |  |
| Age (mean ± SD) | 63.2 ± 6.6* | 62.9 ± 10.1* | 0.937† |
| Gender |  |  |  |
| Female | 3 (25.0) | 38 (55.9) | 0.063‡ |
| Male | 9 (75.0) | 30 (44.1) |  |
| Cell type |  |  |  |
| Adenocarcinoma | 9 (75.0) | 55 (80.9) | 0.698‡ |
| Others | 3 (25.0) | 13 (19.1) |  |
| Size (mean ± SD) | 3.4 ± 1.2* | 3.4 ± 1.9* | 0.999† |
| CD44 | N = 39 | N = 41 |  |
| Age (mean ± SD) | 62.5 ± 9.8* | 63.4 ± 9.6* | 0.704† |
| Gender |  |  |  |
| Female | 16 (41.0) | 25 (61.0) | 0.117‡ |
| Male | 23 (59.0) | 16 (39.0) |  |

TABLE 3-continued

Clinical Characteristics of CD14 and CD44 Expression in Lung Cancer Patients

|  | High (%) | Low (%) | p-value |
|---|---|---|---|
| Cell type | | | |
| Adenocarcinoma | 32 (82.1) | 32 (78.1) | 0.782‡ |
| Others | 7 (18.0) | 9 (22.0) | |
| Size (mean ± SD) | 3.6 ± 1.7* | 3.3 ± 1.8* | 0.393† |

*Data represent as mean ± standard deviation
†Analysis of variance (ANOVA)
‡Fisher's exact test

TABLE 4

Clinical Characteristics of CD14 + CD44 Expression in Lung Cancer Patients

|  | CD44$^{high}$CD14$^+$ | CD44$^{high}$ or CD14$^+$ | CD44$^{low}$CD14$^-$ | p-value |
|---|---|---|---|---|
| CD14 + CD44 | N = 10 | N = 31 | N = 39 | |
| Age (mean ± SD) | 63.1 ± 7.2* | 62.4 ± 10.3* | 63.4 ± 9.8* | 0.922† |
| Gender | | | | |
| Female | 3 (30.0) | 13 (41.9) | 25 (64.1) | 0.062‡ |
| Male | 7 (70.0) | 18 (58.1) | 14 (35.9) | |
| Cell type | | | | |
| Adenocarcinoma | 7 (70.0) | 27 (87.1) | 30 (76.9) | 0.382‡ |
| Others | 3 (30.0) | 4 (12.9) | 9 (23.1) | |
| Size (mean ± SD) | 3.7 ± 1.1* | 3.5 ± 1.9* | 3.3 ± 1.8* | 0.827† |

*Data represent as mean ± standard deviation
†Analysis of variance (ANOVA)
‡Fisher's exact test The expression levels of CD14 in tumor cells were scored and dichotomized to positive or negative CD14 protein expression categories. The expression levels of CD44 in tumor cells were scored and dichotomized to high (score ≥median risk score) or low (score <median risk score) CD44 protein expression categories. Multivariable Cox proportional hazards regression analyses were used to evaluate the associations of various independent prognostic factors with patient survival (Table 5).

TABLE 5

Multivariate Cox Proportional Hazards Regression Analysis with Covariates Age, Gender, Cell type and Tumor Size for Overall survival of Cancer Stem Cell Markers

|  | Hazard ratio | 95% HR C.I. | | p-value* |
|---|---|---|---|---|
| CD14 | | | | |
| CD14 | 2.79 | 1.29 | 6.03 | 0.009 |
| Age | 0.99 | 0.96 | 1.03 | 0.664 |
| Gender | 1.54 | 0.78 | 3.03 | 0.217 |
| Cell type† | 0.76 | 0.36 | 1.62 | 0.478 |
| Size | 1.20 | 1.05 | 1.37 | 0.009 |
| CD44 | | | | |
| CD44 | 9.25 | 3.78 | 22.64 | <0.0001 |
| Age | 1.00 | 0.97 | 1.03 | 0.998 |
| Gender | 1.38 | 0.70 | 2.73 | 0.351 |
| Cell type† | 0.80 | 0.37 | 1.72 | 0.564 |
| Size | 1.11 | 0.97 | 1.27 | 0.128 |
| Combination of CD14 and CD44 | | | | |
| CD14 + CD44 | 3.33 | 2.12 | 5.24 | <0.0001 |
| Age | 0.99 | 0.96 | 1.02 | 0.534 |
| Gender | 1.32 | 0.67 | 2.60 | 0.425 |
| Cell type† | 0.90 | 0.42 | 1.92 | 0.775 |
| Size | 1.17 | 1.02 | 1.34 | 0.022 |

*Wald test for hazard ratio in Cox proportional hazards regression
95% CI: 95% confidence interval
†adenocarcinoma compared with other cell types (reference group)

Results revealed that the independent prognostic factors included CD14 expression (hazard ratio (HR)=2.79, 95% CI=1.29 to 6.03; P=0.009, Cox proportional hazards regression analysis) and CD44 expression (HR=9.25, 95% CI=3.78 to 22.64; P<0.0001, Cox proportional hazards regression analysis). The independent prognostic factors associated with metastasis were CD14 expression (HR=2.63, 95% CI=1.09 to 6.35; P=0.032, proportional hazards regression analysis) and CD44 expression (HR=5.89, 95% CI=2.17 to 16.01; P<0.0001, Cox proportional hazards regression analysis, Table 6).

TABLE 6

Multivariate Cox Proportional Hazards Regression Analysis with Covariates Age, Gender, Cell type and Tumor Size for Relapse free survival of Cancer Stem Cell Markers

|  | Hazard ratio | 95% HR C.I. | | p-value* |
|---|---|---|---|---|
| CD14 | | | | |
| CD14 | 2.63 | 1.09 | 6.35 | 0.032 |
| Age | 1.01 | 0.97 | 1.06 | 0.565 |
| Gender | 2.28 | 0.94 | 5.49 | 0.067 |
| Cell type† | 1.35 | 0.46 | 3.92 | 0.585 |
| Size | 1.05 | 0.85 | 1.28 | 0.670 |
| CD44 | | | | |
| CD44 | 5.89 | 2.17 | 16.01 | 0.001 |
| Age | 1.02 | 0.98 | 1.07 | 0.362 |
| Gender | 2.35 | 1.00 | 5.55 | 0.050 |
| Cell type† | 1.55 | 0.53 | 4.57 | 0.423 |
| Size | 0.96 | 0.77 | 1.19 | 0.684 |
| Combination of CD14 and CD44 | | | | |
| CD14 + CD44 | 2.88 | 1.68 | 4.94 | 0.0001 |
| Age | 1.02 | 0.97 | 1.07 | 0.490 |
| Gender | 2.02 | 0.85 | 4.81 | 0.112 |

TABLE 6-continued

Multivariate Cox Proportional Hazards Regression Analysis with
Covariates Age, Gender, Cell type and Tumor Size for Relapse
free survival of Cancer Stem Cell Markers

|  | Hazard ratio | 95% HR C.I. | | p-value* |
|---|---|---|---|---|
| Cell type† | 1.59 | 0.54 | 4.65 | 0.401 |
| Size | 1.00 | 0.81 | 1.25 | 0.973 |

*Wald test for hazard ratio in Cox proportional hazards regression
95% CI: 95% confidence interval
†adenocarcinoma compared with other cell types (reference group)

Analysis of the individual and combined effects of CD44 and CD14 expression levels on patient prognoses revealed that patients with high-level expression of both CD44 and CD14 in tumor cells demonstrated the worst overall (CD44+CD14, P<0.0001, Kaplan-Meier analysis; FIG. 2, panel B; HR=3.33, 95% CI=2.12 to 5.24; P<0.0001, Cox proportional hazards regression analysis; Table 5) and relapse-free survival (CD14+CD44, P<0.05, Kaplan-Meier analysis; FIG. 2, panel C; HR=2.88, 95% CI=1.68 to 4.94; P=0.0001, Cox proportional hazards regression analysis; Table 6) compared to those with low-level expression of CD44 and CD14 in tumor cells. These results further demonstrate that CD44 and/or CD14 provide a novel prognostic index for predicting metastasis (P=0.0001, Cox proportional hazards regression analysis) and overall survival (P<0.0001, Cox proportional hazards regression analysis) in early stage NSCLC patients (Table 5 and Table 6). These results indicated that patients with high-level expression CD14 and/or CD44 in tumor cells demonstrated significantly poorer overall survival and relapse-free survival compared with patients with low-level expression.

Example 3

Co-Culture with CAFs Led to Enrichment of CD44$^+$CD14$^+$ Lung Cancer Stem Cells Materials and Methods
Immunofluorescence Microscopy Cells were fixed with 4% paraformaldehyde in phosphate buffered saline (PBS) at room temperature. A standard immunofluorescence protocol was followed. Blocking and hybridization were performed in 3% (wt/vol) bovine serum albumin (BSA) in PBS. Monoclonal antibodies (mAbs) targeting Nanog (ReproCELL; 1:300), CD90 FITC-conjugated (5E10; BD Pharmingen; 1:100), CD44 FITC-conjugated (G44-26; BD Pharmingen; 1:10), and CD14 PE-conjugated (HCD14; Biolegend; 1:20) antibodies, were used. The stained cells were examined using an Axiovert 200 microscope (Carl Zeiss, Göttingen, Germany), and a confocal laser scanning microscope (C1si, Nikon, Japan) with MetaXpress® (Molecular Devices).

Western Blot Analyses

The detailed procedures were performed according to standard procedures. The primary antibodies for Nanog (D73G4; 1:1000) were purchased from Cell Signaling Technology, Inc., the primary antibody for CD44 (MAB4073; 1:1000) was purchased from Cell marque and the primary antibody for CD14 (EPR3653; 1:1000) was purchased from Cell marque. Monoclonal mouse anti-β-actin (Chemicon, Millipore; 1:5000) was used as a loading control. The membranes were then washed three times with TBST, followed by incubation with horseradish peroxidase (HRP)-conjugated secondary antibody (1:5,000) in TBST/2% skim milk. Bound antibody was detected using the Enhanced Chemiluminescence System (Santa Cruz, CA). Chemiluminescent signals were captured using the Fujifilm LAS 3000 system (Fujifilm, Tokyo, Japan). All experiments were performed at least three times in duplicate.

Ultra-Low Sphere Forming Assay

An ultra-low sphere-forming assay was performed according to standard procedures and modified as described herein. A single-cell suspension of lung CSCs in MCDB201 serum-free medium (Invitrogen) supplemented with 20 ng/ml EGF (Sigma) and 20 ng/ml bFGF (Invitrogen) was seeded in ultra-low adherent 24-well plates (Corning, Corning, NY, USA; 200 viable cells/well). The medium was supplemented with fresh growth factors twice weekly. After 3 weeks, the spheres were examined under the Axiovert 200 microscope.

Results

Figure 3:
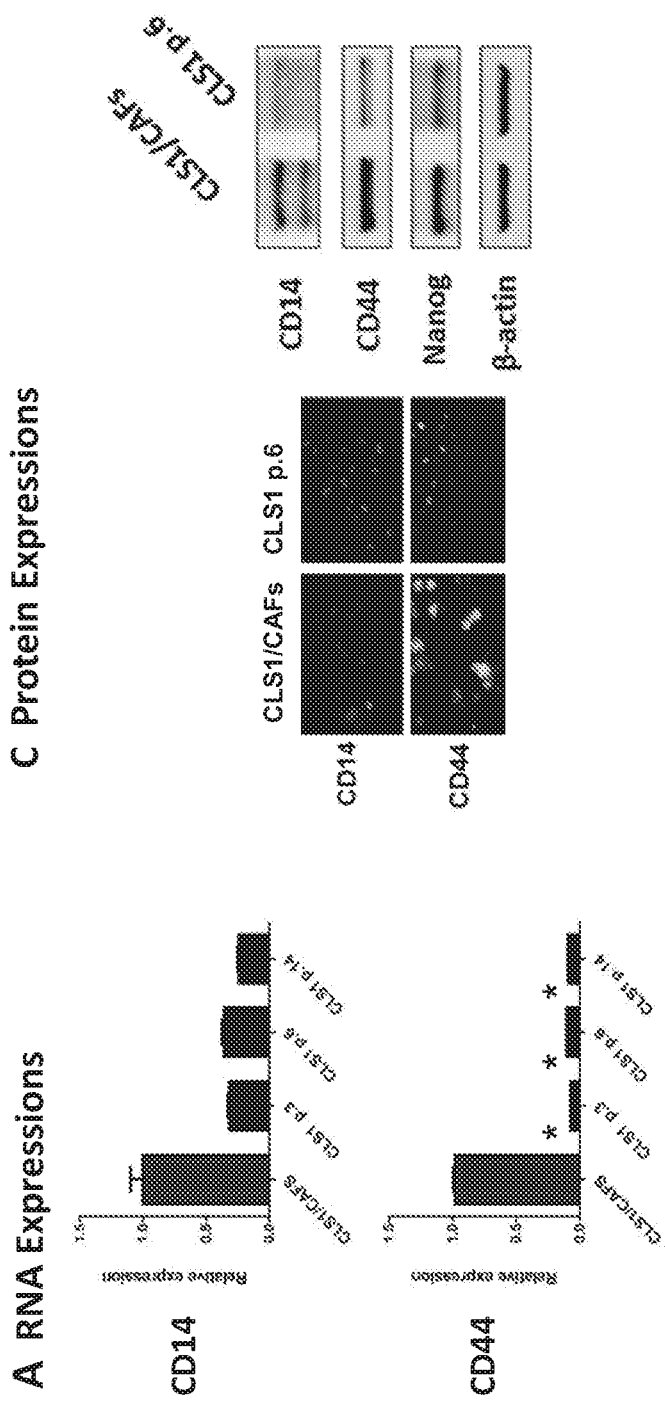
FIG. 3 shows enrichment of CD44 and CD14 on the cell surface of cancer cells co-cultured with CAFs feeder cells. A: RT Q-PCR validation of the CD44 and CD14.CLS1 cells were derived from CLS1 spheres, dissociated to single cells and then sub-cultured without CAFs for different numbers of passages (p3, p6 and p14). The CAFs served as the feeder cell control. The data represent the mean±S.E.M (N=3). B: RT Q-PCR analysis of CD44, CD14 and Nanogin cancer cell (EKVX) cultured with or without CAFs obtained from patients (N=4 patients). The results showed a significant difference of cancer cells which co-cultured with different patient's NFs or CAFs (L2, L5 and L8) in MANOVA test. C: Protein expression of CD44 and CD14 in CLS1 cells cultured with (CLS1/CAF) or without CAFs (CLS1p.6) were estimated via immunofluorescence staining (panel-left) and western blot analysis (panel-right). D: RT Q-PCR analysis was performed to assess expression of the stemness markers Nanog and Oct3/4 in $CD14^+CD44^{Hi}$, $CD14^-CD44^{Hi}$ and $CD14^-CD44^{low}$ populations sorted from primary lung cancer cell (CL152 cells) (N=3). E: The sphere-forming ability (lower panel) and morphology (upper panel) of $CD14^+CD44^{Hi}$, $CD14^-CD44^{Hi}$ and $CD14^-CD44^{low}$ populations sorted from primary lung cancer cell (CL152 cells) after culturing in MCDB201 medium with EGF (20 ng/ml) and bFGF (20 ng/ml) for 21 days. Scale bar, 100 μm. F: The incidence of mouse xenograft tumors from $CD14^+CD44^{hi}$, $CD14^-CD44^{hi}$ and $CD14^-CD44^{low}$ populations sorted from CLS1 lung cancer cell (N≥3 mice) was determined following the subcutaneous injection of different cell numbers ($1\times10^2$ and 10 cells) into NSG mice. The tumor-initiating frequency of CSCs (TIF) was calculated using the L-calclimiting dilution analysis software. CI, confidence interval.
Figure 3:
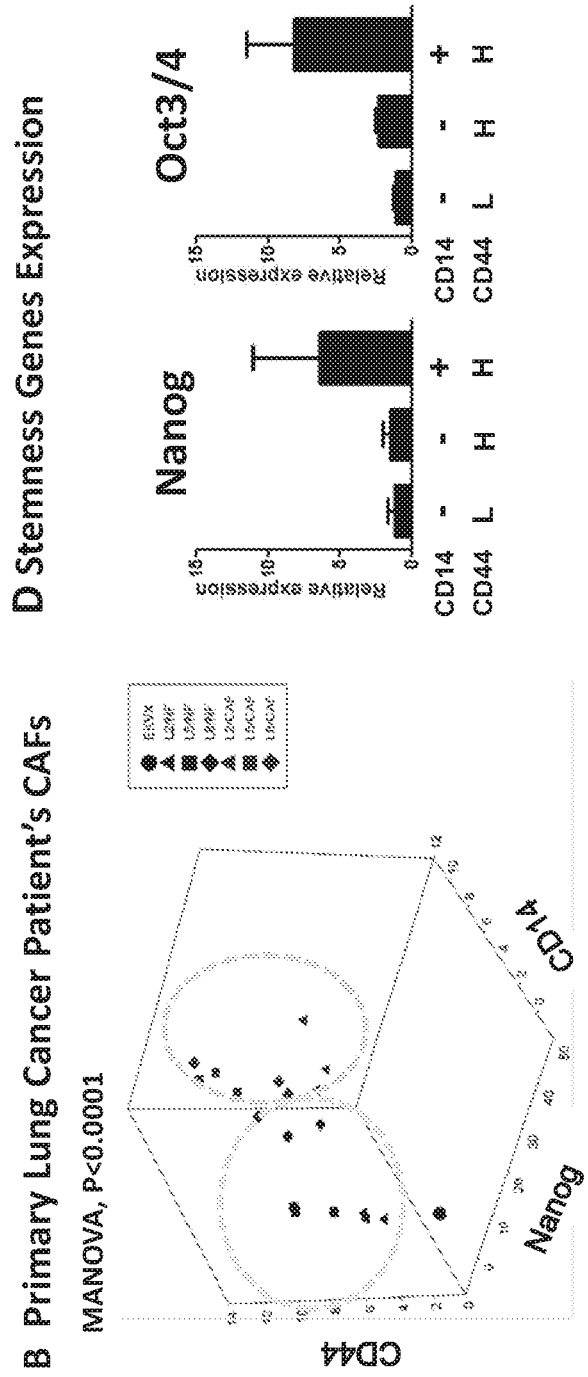
Figure 3:
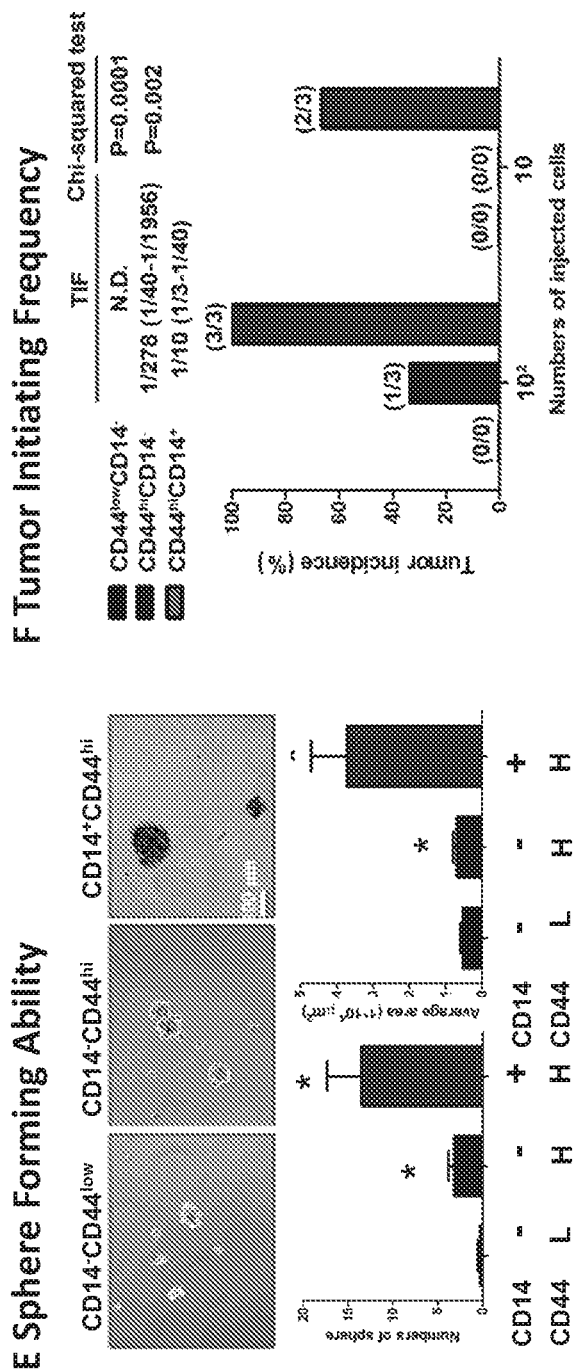

To validate that the expression of CD14 and CD44 would be enhanced in the CSCs/CAF co-culture model as relative to differentiated cancer cells, the gene expression profile of CLS1/CAFs was compared to the gene expression profile of CLS1-differentiated cancer cells cultured without feeder cells through different passages. The comparison demonstrated that the co-culture of CAFs with CLS1 cells induced the expression of CD14 and CD44 compared to cancer cells sub-cultured without CAFs (FIG. 3, panel A).

Figure 5:
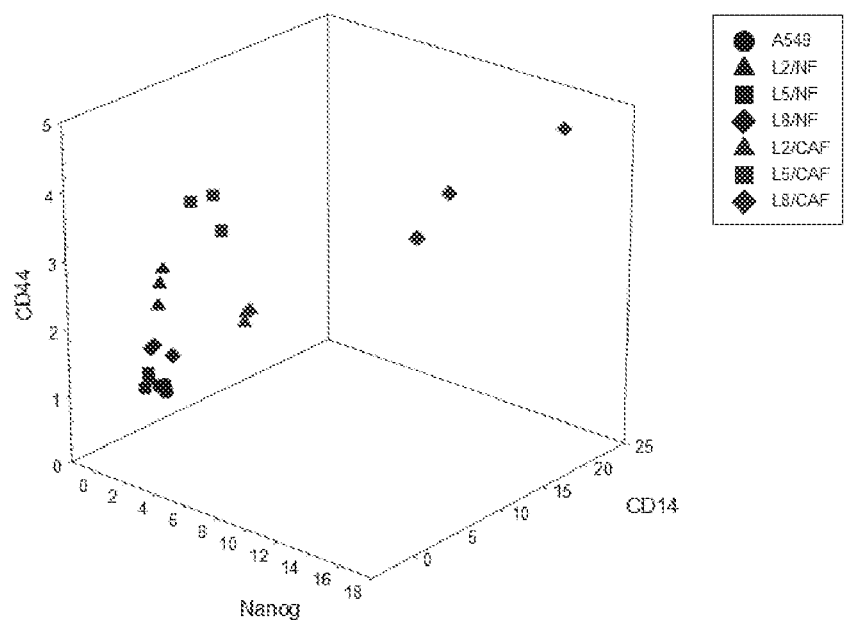
FIG. 5 shows enrichment of CD44, CD14 and Nanog on the cell surface of cancer cells co-cultured with CAFs feeder cells. A: Laser-captured colony cell analysis of CD44, CD 14 and Nanog in cancer cells (A549) cultured with or without CAFs obtained from patients (N=3 patients). B: Flow cytometric analysis of CD44 and CD14 in CLS1 cells cultured with or without CAF feeder cells.
Figure 5:
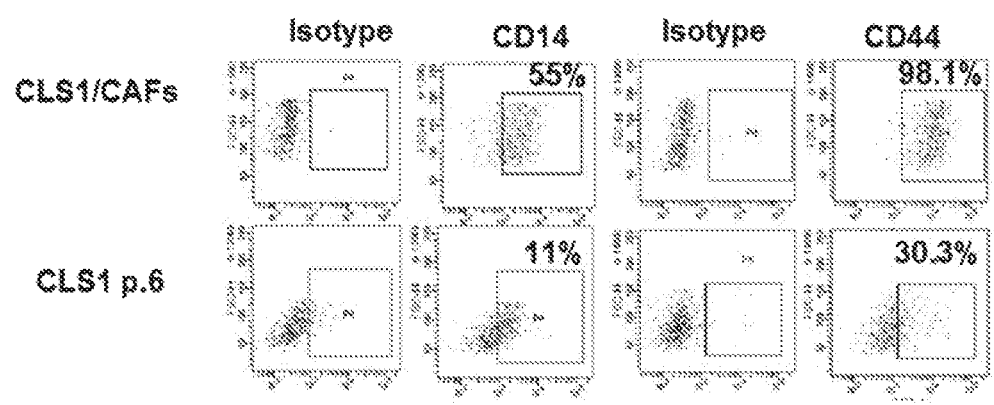

To further evaluate whether CD14 and CD44 was increased in lung cancer cells that were co-cultured with various tumor-derived CAFs, CAFs were isolated from different lung cancer patients. Laser-captured colony cells from different cancer cell lines (A549 and EKVX cells) showed higher expression levels of CD14 and CD44 (FIG. 3, panel B and FIG. 5, panel A). Characteristics of the 12 CAF samples isolated from patients are shown in Table 7.

TABLE 7

Patient Demographics, Tumor Stage, Pathological Diagnosis

| Patient | Age | Sex | TNM | Stage | Histology | Primary cultured cell |
|---|---|---|---|---|---|---|
| L2 | 47 | F | T2aN0 | IIA | ADC | CAFs and NFs |
| L5 | 72 | M | T2bN0 | IIA | ADC | CAFs and NFs |
| L8 | 84 | M | T4N0 | IIIB | SCC | CAFs and NFs |
| CLS1 | 87 | M | T2N0 | IIIA | ASC | Cancer cells and CAFs |

Figure 6:
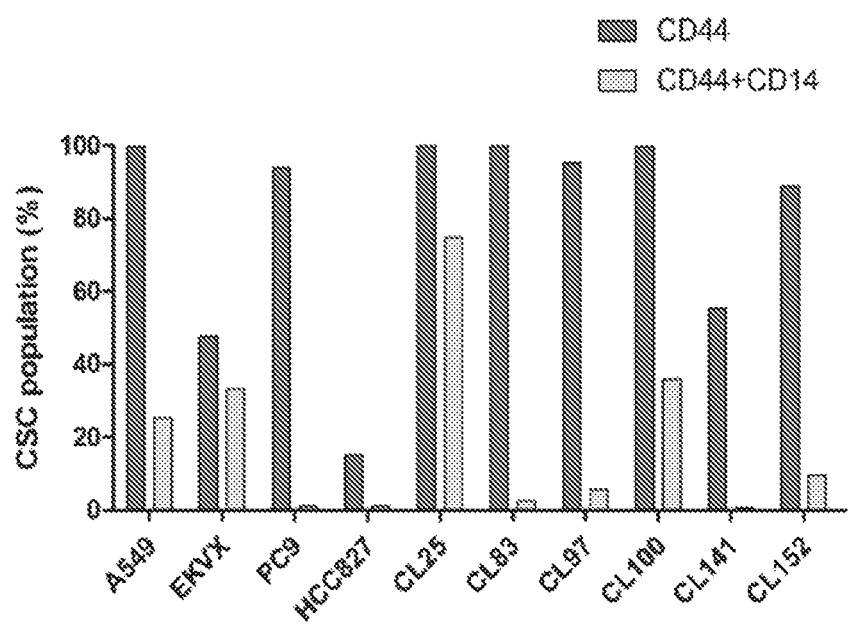
FIG. 6 shows flow cytometry analysis of CD44 and CD14 on the cell surface of cancer cells. CD44 and CD14 doubly stained double positive population in different lung cancer cell lines (A549, EKVX, PC9 and HCC827) and primary lung cancer cells (CL25, CL83, CL97, CL100, CL141 and CL152) was analyzed.

Immunofluorescence staining and Western blotting confirmed that CD14 and CD44 was predominantly expressed in lung CSCs (CLS1/CAFs) rather than differentiated CLS1 cells (FIG. 3, panel C). Flow cytometry analysis showed that CD44 and CD14 were expressed at higher levels in lung CSCs (CLS1/CAFs) (CD14:55%; CD44:98.1%) and the expression levels of CD44 and CD14 were reduced after differentiation (CD14:11%; CD44:30.3%) (FIG. 5, panel B). The percentages of the CD44 positive population and the CD14/CD44 double positive population in different lung cancer cell lines (A549, EKVX, PC9 and HCC827) and primary lung cancer cells (CL25, CL83, CL97, CL100, CL141 and CL152) were determined and the results demonstrated that the CD44 positive population was abundant in different lung cancer cells (79.6±29.7%). FIG. 6. The percentage of CD44/CD14 double positive population was significantly reduced in those cancer cells (19.0±23.9%). This analysis reveals that CD44 and CD14 sufficiently represent a cancer stem cell marker in the tumor niche.

Example 4

CD44$^{Hi}$ CD14$^+$ Cancer Cells Have Higher Tumor Initiating Frequency

Materials and Methods
Flow Cytometry

Population of cancer stem cell markers was analysis and sorted by flow cytometry. Antibodies for the human antigens CD44 FITC-conjugated (G44-26; BD Pharmingen; 1:10) and CD14 PE-conjugated (HCD14; Biolegend; 1:20) were purchased commercially. Lung cancer cell lines and primary lung cancer cells were stained by CD14 and CD44 double staining in PBS at room temperature for 30 minutes. After 30 minutes, stained cells were washed of excess unbound antibodies and resuspended in sorting buffer (1 mM EDTA and 2% FBS in PBS). Flow sorting was done using a BD FACSAriaIII cell sorter (Becton Dickinson), and analysis was done on a FACSCalibur (BectonDickinson). For sorting sample cell to ensure single cell sorting, cell aggregates were eliminated by forward-scatter height versus forward-scatter width (FSC-H versus FSC-W) and side-scatter area versus side-scatter width (SSC-A versus SSC-W). Dead cells were eliminated by excluding propidium iodide (PI, dead cell stain, Molecular Probes) cells, which increased the efficiency of sorting robust, live cells for single-cell experiments.

Results

The tumor initiating ability, which represents the operational definition of a cancer stem cell, of the CD44$^{Hi}$CD14$^+$ population in lung cancer cell lines and primary lung cancer cells was measured. Sorted lung cancer cells (CLS1 cells) were injected subcutaneously at limiting dilutions (1×10$^4$, 1×10$^3$, and 1×10$^2$ cells/mice) into NOD/SCID/IL2Rγ_(NSG) mice. The CD44$^{Hi}$CD14$^+$ population sorted from the lung cancer cell line (CLS1) showed higher tumor-initiating frequency (1/10) as compared to the CD44$^{Hi}$CD14$^-$ population (1/278). The CD44$^{low}$CD14$^+$ population was not determined.

Figure 4:
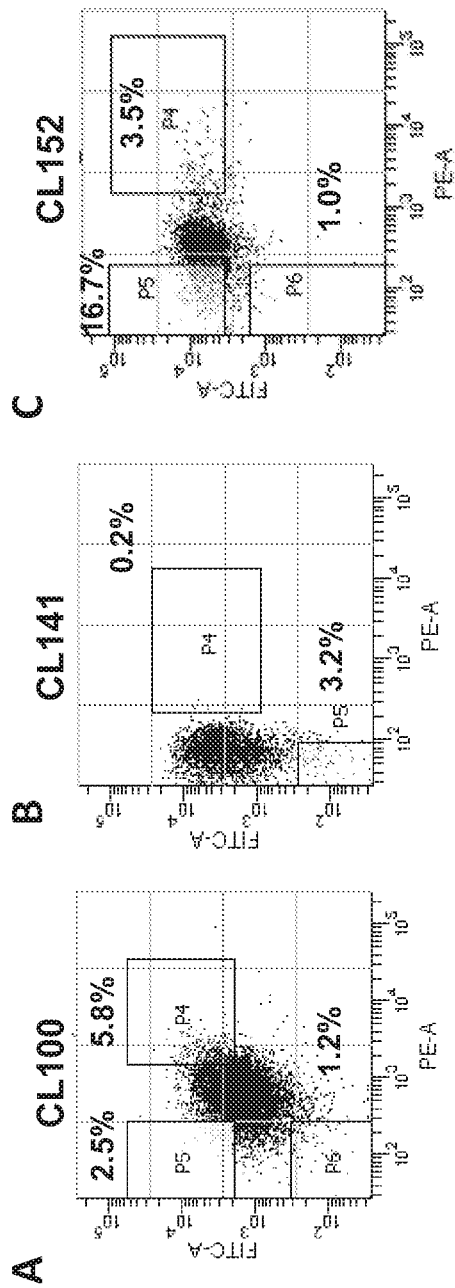
FIG. 4 shows that the $CD14^+CD44^{Hi}$ population sorted from primary lung cancer cells have higher tumor initiating capacity. Upper panel: Flow cytometric analysis of CD44 and CD14, doubly stained in different primary lung cancer cells: CL100 (Panel A), CL141 (Panel B) and CL152 (Panel C). The different primary lung cancer cells showed variable double-positive population (5.8% in CL100, 0.2% in CL141 and 3.5% in CL152 cells). Lower panel: The incidence of mouse xenograft tumors from $CD14^+CD44^{Hi}$, $CD44^{Hi}CD14^-$ and $CD14^-CD44^{low}$ populations sorted from primary lung cancer cell: CL100 (Panel D), CL141 (Panel E), and CL152 (Panel F), (N=6 mice) was determined following the subcutaneous injection of different cell numbers ($1\times10^4$, $1\times10^3$, and $1\times10^2$ cells) into SCID mice. The tumor-initiating frequency of CSCs (TIF) was calculated using the L-calc limiting dilution analysis software. CI, confidence interval.
Figure 4:
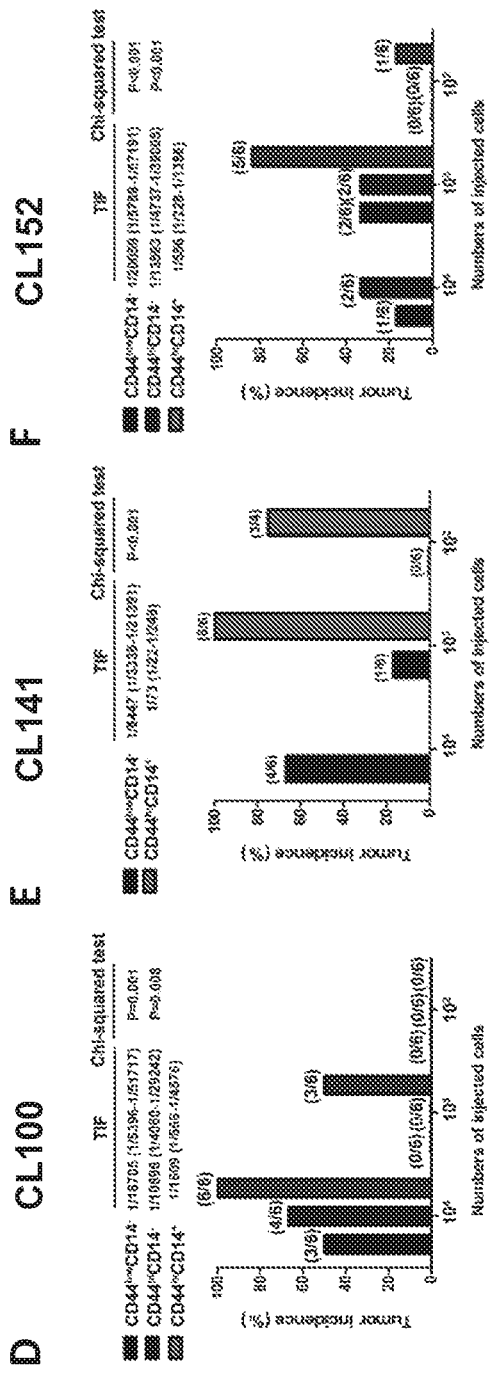

The tumor initiating frequency of the CD44$^{Hi}$CD14$^+$ population sorted from lung cancer cell lines (CLS1 and A549 cells) and primary lung cancer cells (CL100, CL141 and CL152) was also measured. The cell populations were subcutaneously injected at limiting dilutions (1×10$^4$, 1×10$^3$, and 1×10$^2$ cells/mice) into SCID mice. The CD44$^{Hi}$CD14$^+$ population demonstrated higher tumor-initiating frequency in xenografts as compared to cancer cells from the CD44$^{Hi}$CD14$^-$ and CD44$^{low}$CD14$^-$ population (Table 8 and FIG. 4, panels A-F). These results suggest that the CD44$^{Hi}$CD14$^+$ population of lung cancer cells may be tumorigenic stem-like cells.

TABLE 8

TICs Frequency of Cancer Cells Sorted by CSC Markers

| Cell line | Group | Number of injected cells | Tumor incidence | TIF | Chi-squared test |
|---|---|---|---|---|---|
| A549 | CD44$^{Hi}$CD14$^+$ | 1 × 10$^4$ | 6/6 | 1/670 | |
| | CD44$^{Hi}$CD14$^+$ | 1 × 10$^3$ | 4/6 | (1/271-1/1652) | |
| | CD44$^{Hi}$CD14$^+$ | 1 × 10$^2$ | 2/6 | | |
| | CD44$^{Hi}$CD14$^-$ | 1 × 10$^4$ | 4/6 | 1/4119 | P = 0.003 |
| | CD44$^{Hi}$CD14$^-$ | 1 × 10$^3$ | 4/6 | (1/1692-1/10028) | |
| | CD44$^{Hi}$CD14$^-$ | 1 × 10$^2$ | 1/6 | | |
| | CD44$^{Low}$CD14$^-$ | 1 × 10$^4$ | 2/3 | 1/4248 | P = 0.005 |
| | CD44$^{Low}$CD14$^-$ | 1 × 10$^3$ | 3/6 | (1/1393-1/12952) | |
| | CD44$^{Low}$CD14$^-$ | 1 × 10$^2$ | 0/4 | | |
| CLS1 | CD44$^{Hi}$CD14$^+$ | 1 × 10$^4$ | 6/6 | 1/670 | |
| | CD44$^{Hi}$CD14$^+$ | 1 × 10$^3$ | 4/6 | (1/271-1/1652) | |
| | CD44$^{Hi}$CD14$^+$ | 1 × 10$^2$ | 2/6 | | |
| | CD44$^{Hi}$CD14$^-$ | 1 × 10$^4$ | 4/6 | 1/5685 | P = 0.005 |
| | CD44$^{Hi}$CD14$^-$ | 1 × 10$^3$ | 5/6 | (1/2352-1/13740) | |
| | CD44$^{Hi}$CD14$^-$ | 1 × 10$^2$ | 1/6 | | |
| | CD44$^{Low}$CD14$^-$ | 1 × 10$^4$ | 6/6 | 1/4326 | P = 0.007 |
| | CD44$^{Low}$CD14$^-$ | 1 × 10$^3$ | 0/6 | (1/1784-1/10489) | |
| | CD44$^{Low}$CD14$^-$ | 1 × 10$^2$ | 0/6 | | |

The tumor-initiating frequency of CSCs (TIFC) was calculated using the L-calc limiting dilution analysis website.
CI, confidence interval;
N.D., not determined.
Chi-squared test was analyzed for the CD44$^{Hi}$CD$^-$ and CD44$^{Low}$CD14$^-$ test groups.

The transcriptomic and proteomic analysis described herein identified that CD14 and/or CD44 were present at higher levels in CSC/CAF co-cultures as compared to CAF cultures. Any of the proteins identified herein, may be used as a biomarker (individually or in combination) for lung cancer stem cells, for example in methods for determining presence of lung cancer stem cells in a sample, identifying patients having lung cancer associated with poor prognosis, selecting a candidate for treatment, monitoring lung cancer progression, assessing the efficacy of a treatment against the lung cancer, determining a course of treatment, assessing whether a subject is at risk for a relapse of the lung cancer, and/or for research purposes, including, e.g., studying the mechanism of lung cancer and/or biological pathways/processes involved in lung cancer, which may be relied upon for the development of new therapies.

Example 5

Expression of CD14 on Various Types of Cancel Stem Cells

Various types of cancer cells, including liver cancer cells, colon cancer cells, and pancreatic cancer cells, were stained with a PE-conjugated anti-CD14 antibody (HCD14; Biolegend; 1:20 in PBS) at room temperature for 30 minutes, following manufacturer's protocol. An isotype antibody was used as a negative control for non-specific bindings. The cells were then washed by PBS to remove unbound antibodies, re-suspended in a sorting buffer (1 mM EDTA and 2% FBS in PBS) PBS, and subject to fluorescence-activated cell sorting (FACS) analysis, using a cell sorter of BD FACSAsia™ Fusion (Becton Dickinson).

As shown in Table 9 below, CD14 expression was observed on various types of cancer cells.

TABLE 9

CD14 Expression in Various Types of Cancer Cell Lines

| Cell lines | Cancer Type | CD14 (%) |
|---|---|---|
| Huh7 | Hepatocarcinoma Cells | 10.3 |
| HCT116 | Colorectal carcinoma | 0.9 |
| MiaPaca2 | Pancreas carcinoma | 9.2 |
| BXPC3 | Pancreas adenocarcinoma | 9.8 |

The results of this study indicate that CD14 can be used as a biomarker for various types of cancer cells, e.g., cancer stem cells.

OTHER EMBODIMENTS

All of the features disclosed in this specification may be combined in any combination. Each feature disclosed in this specification may be replaced by an alternative feature serving the same, equivalent, or similar purpose. Thus, unless expressly stated otherwise, each feature disclosed is only an example of a generic series of equivalent or similar features. From the above description, one skilled in the art can easily ascertain the essential characteristics of the present disclosure, and without departing from the spirit and scope thereof, can make various changes and modifications of the present disclosure to adapt it to various usages and conditions. Thus, other embodiments are also within the claims.

EQUIVALENTS AND SCOPE

Those skilled in the art will recognize, or be able to ascertain using no more than routine experimentation, many equivalents to the specific embodiments of the present disclosure described herein. The scope of the present disclosure is not intended to be limited to the above description, but rather is as set forth in the appended claims.

In the claims articles such as "a," "an," and "the" may mean one or more than one unless indicated to the contrary or otherwise evident from the context. Claims or descriptions that include "or" between one or more members of a group are considered satisfied if one, more than one, or all of the group members are present in, employed in, or otherwise relevant to a given product or process unless indicated to the contrary or otherwise evident from the context. The present disclosure includes embodiments in which exactly one member of the group is present in, employed in, or otherwise relevant to a given product or process. The present disclosure includes embodiments in which more than one, or all of the group members are present in, employed in, or otherwise relevant to a given product or process.

Furthermore, the present disclosure encompasses all variations, combinations, and permutations in which one or more limitations, elements, clauses, and descriptive terms from one or more of the listed claims is introduced into another claim. For example, any claim that is dependent on another claim can be modified to include one or more limitations found in any other claim that is dependent on the same base claim. Where elements are presented as lists, e.g., in Markush group format, each subgroup of the elements is also disclosed, and any element(s) can be removed from the group. It should it be understood that, in general, where the present disclosure, or aspects of the present disclosure, is/are referred to as comprising particular elements and/or features, certain embodiments of the present disclosure or aspects of the present disclosure consist, or consist essentially of, such elements and/or features. For purposes of simplicity, those embodiments have not been specifically set forth in haec verba herein. It is also noted that the terms "comprising" and "containing" are intended to be open and permits the inclusion of additional elements or steps. Where ranges are given, endpoints are included. Furthermore, unless otherwise indicated or otherwise evident from the context and understanding of one of ordinary skill in the art, values that are expressed as ranges can assume any specific value or sub-range within the stated ranges in different embodiments of the present disclosure, to the tenth of the unit of the lower limit of the range, unless the context clearly dictates otherwise.

This application refers to various issued patents, published patent applications, journal articles, and other publications, all of which are incorporated herein by reference. If there is a conflict between any of the incorporated references and the instant specification, the specification shall control. In addition, any particular embodiment of the present disclosure that falls within the prior art may be explicitly excluded from any one or more of the claims. Because such embodiments are deemed to be known to one of ordinary skill in the art, they may be excluded even if the exclusion is not set forth explicitly herein. Any particular embodiment of the present disclosure can be excluded from any claim, for any reason, whether or not related to the existence of prior art.

Those skilled in the art will recognize or be able to ascertain using no more than routine experimentation many equivalents to the specific embodiments described herein. The scope of the present embodiments described herein is not intended to be limited to the above Description, but rather is as set forth in the appended claims. Those of ordinary skill in the art will appreciate that various changes and modifications to this description may be made without departing from the spirit or scope of the present disclosure, as defined in the following claims.

What is claimed is:

1. A method for analyzing a sample and treating a human patient, the method comprising:
   (i) providing a sample suspected of containing cancer stem cells, wherein the sample is a biological sample of a human patient having cancer,
   (ii) measuring the level of CD14 and the level of CD44 in the sample,
   (iii) comparing the level of CD14 and the level of CD44 measured in step (ii) with a predetermined level of CD14 and a predetermined level of CD44, respectively; wherein the predetermined level of CD14 and the predetermined level of CD44 represent a level of CD14 and a level of CD44, respectively, in a population of subjects who do not have the cancer;
   (iv) determining presence of cancer stem cells in the sample, wherein a combination of an elevated level of CD14 and an elevated level of CD44 relative to the predetermined level of CD14 and the predetermined level of CD44, respectively, is indicative of presence of cancer stem cells in the sample, and
   (v) performing a cancer treatment to the human patient, who is identified as having presence of cancer stem cells as determined in step (iv); wherein the cancer treatment is selected from the group consisting of chemotherapy, radiation therapy, immunotherapy, and surgical therapy.

2. The method of claim 1, wherein step (ii) comprises measuring the level of CD14 protein and/or the level of CD44 protein.

3. The method of claim 2, wherein step (ii) is performed to measure the level of the CD14 protein and the level of CD44 protein in soluble form or expressed on cell surface.

4. The method of claim 2, wherein the level of CD14 protein and the level of CD44 protein are measured by an immunohistochemical assay, an immunoblotting assay, or a flow cytometry assay.

5. The method of claim 1, wherein step (ii) comprises measuring the level of a nucleic acid encoding CD14 and/or the level of a nucleic acid encoding CD44.

6. The method of claim 5, wherein the level of nucleic acid encoding CD14 and the level of nucleic acid encoding CD44 are measured by a real-time reverse transcriptase PCR (RT-PCR) assay or a nucleic acid microarray assay.

7. The method of claim 1, wherein the biological sample is a body fluid sample or a tissue sample.

8. The method of claim 7, wherein the tissue sample is obtained from a tumor site or a suspected tumor site.

9. The method of claim 1, wherein the human patient has non-small-cell-lung-cancer (NSCLC).

10. The method of claim 1, wherein the human patient has lung cancer, liver cancer, colon cancer, or pancreatic cancer.

11. The method of claim 1, wherein the cancer treatment comprises a chemotherapeutic agent or an immunotherapeutic agent.

12. The method of claim 11, wherein the cancer treatment comprises the chemotherapeutic agent, which is selected from the group consisting of carboplatin, cisplatin, docetaxel, gemcitabine, nab-paclitaxel, paclitaxel, pemetrexed, and vinorelbine.

* * * * *

SEQUENCE LISTING

<160> NUMBER OF SEQ ID NOS: 10

<210> SEQ ID NO 1
<211> LENGTH: 20
<212> TYPE: DNA
<213> ORGANISM: Artificial Sequence
<220> FEATURE:

-continued

<223> OTHER INFORMATION: Synthetic Polynucleotide

<400> SEQUENCE: 1
ttcagccaaa cgaccatctg                                                    20

<210> SEQ ID NO 2
<211> LENGTH: 21
<212> TYPE: DNA
<213> ORGANISM: Artificial Sequence
<220> FEATURE:
<223> OTHER INFORMATION: Synthetic Polynucleotide

<400> SEQUENCE: 2
gaaccacact cggaccacat c                                                  21

<210> SEQ ID NO 3
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 3
caccagtccc aaaggcaaac                                                    20

<210> SEQ ID NO 4
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 4
gccttctgcg tcacaccatt                                                    20

<210> SEQ ID NO 5
<211> LENGTH: 23
<212> TYPE: DNA
<213> ORGANISM: Artificial Sequence
<220> FEATURE:
<223> OTHER INFORMATION: Synthetic Polynucleotide

<400> SEQUENCE: 5
cacagaggag ggaactgaat gac                                                23

<210> SEQ ID NO 6
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 6
aactcttcgg ctgcctctga                                                    20

<210> SEQ ID NO 7
<211> LENGTH: 24
<212> TYPE: DNA
<213> ORGANISM: Artificial Sequence
<220> FEATURE:
<223> OTHER INFORMATION: Synthetic Polynucleotide

<400> SEQUENCE: 7
tggacactca catgggagtc aaga                                               24

```
<210> SEQ ID NO 8
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 8
cgactgttga ctgcaatgca                                               20

<210> SEQ ID NO 9
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 9
ctggaacggt gaaggtgaca                                               20

<210> SEQ ID NO 10
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 10
cggccacatt gtgaactttg                                               20
```